United States Patent [19]
Grinnell

[11] Patent Number: 5,270,168
[45] Date of Patent: Dec. 14, 1993

[54] METHOD FOR DIAGNOSING NON-HEALING ULCERS

[75] Inventor: Frederick Grinnell, Dallas, Tex.

[73] Assignee: Board of Regents, The University of Texas System, Austin, Tex.

[21] Appl. No.: 795,667

[22] Filed: Nov. 21, 1991

Related U.S. Application Data

[63] Continuation-in-part of Ser. No. 483,207, Feb. 21, 1990, abandoned.

[51] Int. Cl.$^5$ .......................... C12Q 1/00; C12Q 1/02
[52] U.S. Cl. ..................................... 435/7.21; 435/7.9; 435/7.92; 435/7.93; 435/7.94; 435/7.95; 435/29; 436/514; 436/515; 436/516; 436/518; 436/548
[58] Field of Search ...................... 435/7.93, 7.94, 7.9, 435/7.92, 7.95, 971, 96, 13, 240.27, 7.21, 29; 436/514, 515, 516, 518, 824, 548, 530; 530/387.1, 388.1, 382, 412

[56] References Cited

U.S. PATENT DOCUMENTS

| | | | |
|---|---|---|---|
| 4,281,061 | 7/1981 | Zuk et al. | 435/7 |
| 4,789,734 | 12/1988 | Pierschbacher | 530/395 |
| 4,894,326 | 1/1990 | Matsuura et al. | 435/7 |
| 4,925,924 | 5/1990 | Silver et al. | 530/356 |
| 4,980,279 | 12/1990 | Peters et al. | 435/7 |

OTHER PUBLICATIONS

Hayashi, M. et al. (1981) "Differences in Domain Structures between Plasma and Cellular Fibronectins", *J. Biol. Chem.*, 256:11292–11300.
Underwood et al. *J. Immunol Methods* v127 (1990) 91–101.
Oikarinen et al. *J. Invest. Dermatol.* vol. 81 (1983) 261–266.
Smith et al. *Ann. Clin. Biochem.* v.18 (1981) 253–274.
Preissner et al. *Blood* v. 71(6) (1988) 1581–1589.
Clemmensen, I. (1981) "Fibronectin and its Role in Connective Tissue Diseases," *European J. of Clinical Investigation*, 11:145–146.
Wysocki, A., et al., ASCB Abstract Form:17 (1989), *J Cell Biol*, 109:138a, Oct., 1989.
Wysocki A., et al., *Arch Dermatol*, 124:175–177 (1988).
Yamada, K. M., et al., *Journal of Cell Biology*, 99:29–36 (1984).
Eliasson, S. G., "Neuropathy and the Diabetic Foot," *The Diabetic Foot*, The C. V. Mosby Co., St. Louis, Mo.: 61–85 (1983).
Juergens, J. L., et al., "Chronic Venous Insufficiency (Postphlebitic Syndrome, Chronic Venous Stasis)", *Peripheral Vascular Disease*, W. B. Saunders Co., Philadelphia, Pa.: 809–821 (1980).
Parish, L. C., et al., "Bedsores Over the Centuries," *The Decubitus Ulcer*, Mason Publishing U.S.A., Inc., New York, N.Y. (date unknown).
Telios Product Brochure, Telios Pharmaceuticals, Inc., San Diego, Calif. (date unknown).
"Clinical Manifestations of Peripheral Vascular Disease": 41–49 (date, author unknown).
Wysocki, A. B. and Grinnell, F., *Laboratory Investigation*, 63(6):825–831 (1990).
Hayman, E. G., et al., *J Cell Biol*, 95:20–23 (1982).
Conlan, M., et al., *Blood*, 72:185–190 (1988).
Preissner, K., *Blut*, 59:419–431 (1989).
Reilly, J. T., *J Clin Pathol*, 41:1269–1272 (1988).

*Primary Examiner*—Sam Rosen
*Attorney, Agent, or Firm*—Arnold, White & Durkee

[57] ABSTRACT

The present invention provides methods for the diagnosis of non-healing ulcers in humans. Provided are methods for detecting the presence of non-healing ulcers by assaying for certain cell adhesion-related proteins or their degradation products in ulcer exudate. The methods of the present invention are useful as an initial, quick and inexpensive screening process for a condition which is often misdiagnosed. It has been discovered that in non-healing ulcers there appear to be proteases which degrade cell adhesion-related proteins, e.g., fibronectin and vitronectin. Protein separation techniques, such as electrophoresis, may be used in combination with immunoassay techniques to isolate and identify these degradation products, as well as the cell adhesion-related proteins themselves.

30 Claims, 10 Drawing Sheets

METHOD FOR DIAGNOSING NON-HEALING ULCERS

The Federal Government may have rights concerning the present invention in view of related research supported by research grants from the National Institutes of Health (GM31321, CA14609, GM21681 and F32-NR06262).

BACKGROUND OF THE INVENTION

This application is a continuation-in-part of U.S. Ser. No. 07/483,207 filed Feb. 21, 1990 now abandoned.

Chronic, non-healing cutaneous ulcers (hereinafter referred to as "ulcers") are a major unresolved health problem. Typically, cutaneous ulcers appear on an extremity, and are often indicative of a secondary disorder, i.e., a peripheral circulatory disorder. Cutaneous ulcers which are secondary to a peripheral circulatory disorder are generally classified as venous stasis ulcers, diabetic ulcers, or decubitus ulcers. Although most ulcers are secondary to a peripheral vascular disease, some are secondary to dermatological, endocrine, hematological, or other systemic diseases.

Venous stasis ulcers are caused by chronic venous insufficiency. Chronic venous insufficiency is a pathological condition of the skin and subcutaneous tissues of the lower extremity that results from prolonged stasis of the venous blood flow. Venous stasis is primarily caused by an abnormal venous hypertension that exists with post phlebitic conditions or with incompetent varicose veins. The elevated venous pressure disrupts the delicate balance between the intravascular and interstitial forces of the capillary bed. Fluid leaves the intravascular compartment and enters the surrounding interstitial tissue. Edema and stasis develop as a result in most instances.

The first observable manifestation of chronic venous insufficiency is usually edema. When the edema has been present for some time, areas of pigment, purpura and petechiae may appear. The longer the edema has been present, the greater the damage, and the greater the tendency for subcutaneous fibrosis to develop, producing areas of induration.

Ulceration is a common disabling complication of chronic venous insufficiency. In many instances, the ulcers develop at the site of minor contusions. In other instances, they develop at areas of dermatitis or chronic induration. Sometimes they follow minor infections in the skin. These ulcers occasionally heal readily, but more often they are chronic, refractory to therapy, and are classified as "non-healing."

Venous stasis ulcers are treated with bed rest and elevation of the legs above the heart level. Pressure is applied to the area of the ulcer, typically by support stockings, to alleviate non-healing in the extremity. Antibiotics are occasionally indicated, especially when the ulcer is surrounded by severe, acute cellulitis. If the ulcer fails to heal spontaneously with these measures, skin grafting may be required. In 1979, there were about 128,000 patients hospitalized primarily for non-healing venous stasis ulcers with an average 11.4 day length of stay, which, at $200 per day, amounted to about $300 million in health care costs.

In contrast to venous stasis ulcers, where there is blood pooling, decubitus ulcers are caused by the ischemic necrosis and ulceration of tissues overlying a bony prominence which has been subject to prolonged pressure. Generally, this pressure is caused by a bed, wheelchair, cast, or splint. Decubitus ulcers are most frequently seen in patients who are debilitated, paralyzed, or otherwise long bedridden. Depending on the patient's position various areas on the patient's body may be affected. However, the feet and sacral areas are most often afflicted. Decubitus ulcers can affect not only superficial tissues, but also muscle and bone.

The most important single precipitating factor for decubitus ulcers is pressure. The pressure impairs local circulation and causes local tissue anoxia that progresses to necrosis of the skin and subcutaneous tissues. Therefore, decubitus ulcers are treated by alleviating the pressure on the afflicted area, and if possible, by lowering the extremity below the heart level to increase circulation to the area. Decubitus ulcers occasionally heal spontaneously; however, decubitus ulcers are more often refractory to therapy and require surgical intervention.

The clinical syndrome of diabetes mellitus involves large vessel disease, microvascular disease, and neuropathy. Diabetics have an abnormality of the capillary basal lamina (basement membrane) characterized by thickening of the lamina of capillary beds of the skin and skeletal muscle. The process affects, among other areas, the legs and feet. Microvascular disease, typically in combination with neuropathy, causes the associated skin and underlying tissue to become anoxic. If the tissue remains anoxic for a sufficient time, the tissue becomes necrotic and cutaneous ulcerations form. Generally, these ulcers occur on the feet or lower extremities. The goal of treatment is often returning circulation to the necrotic area. However, because these ulcers are often refractory to treatment, surgical intervention is frequently required.

Why some cutaneous ulcers heal, while others are chronic and refractory to treatment, is not entirely understood. Presently, clinicians are unable to determine which ulcers will heal readily and which are non-healing and will become chronic. Since, the diagnosis of a non-healing ulcers is not presently feasible, clinicians often waste valuable time and resources attempting to heal ulcers which are refractory to treatment. Clinically, ulcers are characterized as non-healing if they are refractory to therapy and are present for greater than a year, or are progressing towards healing at a rate of less than or equal to 1 millimeter per week.

As discussed above, the treatment of cutaneous ulcers is primarily directed at the underlying pathology. These therapies, although well intentioned, are without much value if the ulcer in question is of the type which is non-healing. Therefore, it is imperative that the clinician properly diagnose the ulcer before commencing treatment. If treatment is erroneously administered (treating a non-healing ulcer conventionally), not only will the patient be discomforted and caused additional expense, but the loss of life or limb may result. Therefore, in order for all cutaneous ulcers to be more effectively treated, thereby reducing patient discomfort, cost, and convalescence time, a method for differentially diagnosing non-healing cutaneous ulcers from readily healing ulcers is needed.

Although chronic skin ulcers continue to present a serious clinical problem (Juergens et al., 1980 *Peripheral Vascular Diseases*, WB Saunders Co. Philadelphia; Crenshaw et al. 1989, J. Rehabil. Res. 26:63-74), the underlying cause(s) responsible for poor wound closure remains unknown. In chronic ulcers, keratinocytes may be unable to migrate over the wound bed because of a defect in the cells or in the wound matrix. Polypeptide growth factors and adhesion proteins play a role in wound epithelization (cf. Clark et al., 1988, *The molecular and cellular biology of wound repair.* Plenum Press New York). Chronic ulcers have been treated by topical application of platelet releasate, which contains both growth factors and adhesion proteins, and early clinical results with this procedure have been promising (Knighton, et al., 1986 Ann. Surg. 204:322-330; Knighton et al., 1990, Surg. Gyn. Obst. 170:56-60).

Fibronectin is an adhesion protein found in blood and many tissues (Mosher D. F., 1989, *Fibronectin,* Academic Press Inc. San Diego)) that is deposited at the wound interface after injury (Grinnell et al, 1981, J. Invest. Dermatol. 76:181-189; Clark et al., 1982, J. Invest. Dermatol., 79:264-269). Both plasma and cellular fibronectin occur in the wound bed (Clark, et al., 1983, J. Invest. Dermatol. 80:26s-30s; French-Constant, et al., J. Cell Biol. 109:903-914). Elevated levels of fibronectin occur in granulation tissue (Grinnell, et al., 1981, J. Invest. Dermatol., 76:181-189; Kurkinen et al., 1980, Lab. Invest., 43:47-51) and persist in a variety of inflammatory states (cf. Grinnell, 1984, J. Cell. Biochem., 26:107-116). Of particular relevance to cutaneous healing, fibronectin promotes keratinocyte migration (O'-Keefe et al., 1985, J. Invest. Dermatol., 85:125-130; Nickoloff, et al., 1988, Am. J. Pathol. 132:543-551), and keratinocytes within wounds transiently activate fibronectin receptor function (Grinnell, 1990, J. Trauma, 30:s144-s149). In clinical studies, topical application of fibronectin has been found to increase epithelization of chronic corneal ulcers (Nishida, 1983, Larch Oppthalmology 101:1046-1048; Kono et al., 1985, J. Rheumatol. 12:487-489) and may also improve epithelization of venous stasis ulcers (Wysocki et al., 1988, Arch. Dermatol., 124:175-177).

The presence of fibronectin fragments in brochoalveolar lavage fluid (Castell, et al., 1988, Biochem. Soc. Trans. 16:378-379) and in tear fluid isolated from chronic corneal ulcers (Barlati et al., 1990, Exp. Eye Res., 51:1-9) showed that fibronectin degradation can occur in the wound bed under some circumstances. Failure of chronic cutaneous ulcers to epithelize properly might result from an alteration or degradation of fibronectin. Consistent with this idea, fibronectin is partially degraded in chronic ulcer fluid but intact in mastectomy fluid and suction blister fluid (see Example 1 and Wysocki et al. Lab. Invest. 63:825-831).

SUMMARY OF THE INVENTION

The present invention is generally directed to methods for the diagnosis of non-healing ulcers. More particularly, the preset invention relates to methods for detecting the presence of non-healing ulcers by assaying certain proteins relating to cell adhesion and/or degradation products of such proteins in ulcer exudate or tissue sections obtained from ulcers. The methods of the present invention are useful as an initial, quick and inexpensive screening process for a condition which is often misdiagnosed. Accordingly, one aspect of the present invention provides a method for the diagnosis of a non-healing ulcer in a human subject by immunologically assaying a tissue sample from the ulcer for cell adhesion-related protein fragments. The assay utilizes the specific cross-reactivity of the cell adhesion-related protein or fragments thereof with monoclonal or polyclonal antibodies directed toward cell adhesion proteins, including human fibronectin or vitronectin. The inventive method is based in part on the discovery that certain proteases are present in the ulcers of patients suffering from non-healing ulcers. These proteases degrade cell adhesion-related proteins, e.g., fibronectin and vitronectin. It is believed that the lack of an intact cell adhesion-related protein or the presence of its degradation products inhibits tissue healing. Tests of the present invention have demonstrated that when these intact cell adhesion-related proteins are not present in the ulcer, a non-healing ulcer is indicated.

According to a preferred embodiment, a combination SDS-gel electrophoresis immunoassay is utilized to determine the presence of intact cell adhesion-related proteins. According to a further preferred embodiment, the instant invention assays a sample collected from the ulcer of a subject to isolate and identify degradation products of a cell adhesion-related protein. Degradation products of fibronectin appear as protein fragments, the most prominent components having molecular weights of about 125 kDa and 93 kDa. Fragments having molecular weights of 200 kDa, 116.5 kDa, 97 kDa, 66 kDa and 43 kDa have also been noted, but with less regularity than the 125 kDa and 93 kDa fragments. Tests of the present invention have shown that the presence of these degradation products in the sample is indicative of a non-healing ulcer. Further tests according to the present invention have demonstrated that electrophoresis, particularly in combination with immunoassay techniques, may be used to isolate and identify these degradation products, as well as the cell adhesion-related proteins themselves. Accordingly, a method is provided wherein the proteins included in the sample are separated by molecular weight on a matrix. The proteins are then stained. The stained separated proteins appear as individual bands of stain on the matrix. The relative position of a particular band is indicative of the presence of a protein having a specific molecular weight. The presence of certain bands of stain (particularly the 125 KDa and 93 KDa bands) is indicative of a non-healing ulcer.

The instant invention further provides a method using electrophoresis in combination with an immunoassay technique to isolate and identify the cell adhesion-related proteins and their degradation products. According to one embodiment of the present invention, a sample is initially obtained from the ulcer of the subject. The proteins included in the sample are then separated by molecular weight using electrophoresis. The separated proteins are reacted with a first antibody which specifically binds a cell adhesion-related protein and its degradation products. After treatment with the first antibody the separated proteins are reacted with a second antibody specifically binding the first antibody. The second antibody is conjugated to a label such as an enzyme, peroxidase for example, which forms a chromophoric product on contact with a substrate (chromophoric precursor) of the enzyme. The separated proteins are then visualized, for example by staining during incubation with substrate. The visualized separated proteins appear as individual bands. The relative position of a particular band is indicative of the presence of a protein having a specific molecular weight. The presence of particular stained bands correspond to the cell adhesion-related proteins and their degradation products, and accordingly, are indicative of the presence of a non-healing ulcer.

Numerous other immunoassays may be applied to determine the presence of adhesion-related protein or protein fragments. For example, a first antibody which specifically binds said protein or protein fragments may be labelled, for example by an enzyme, radioisotope or fluorescent compound. The separated proteins or protein fragments may be reacted with the first antibody and directly visualized. Additionally, after binding of separated proteins by a first antibody, a labelled second antibody may be used which specifically binds the first antibody. Antibodies used may be polyclonal, particularly where a broader specificity is desired, for example, with the first antibody, or monoclonal, particularly when a specific immunologically distinct protein fragment is targeted.

The cell adhesion-related proteins described herein include fibronectin and vitronectin, both present in blood and serum, as well as laminin, collagen types I-IV, fibrin (fibrinogen) and thrombospondin.

In a broader sense, the present invention comprises a method for the diagnosis of a non-healing ulcer in a human subject. The method involves assaying a fluid sample (preferably ulcer exudate) from an ulcer of said subject for an intact cell adhesion-related protein and fragments thereof. The preferred cell adhesion-related protein is fibronectin although vitronectin or other proteins may suffice for particular conditions. Absence of an intact cell adhesion-related protein or presence of cell adhesion-related protein fragments are indicative of a non-healing ulcer.

Assaying the fluid sample preferably involves interaction of the fluid with an antibody specifically binding said cell adhesion-related protein or fragments thereof. Polyclonal antibodies are desirable for broad specificity and monoclonal for narrower specificity. The non-healing ulcer is, for example, a venous stasis ulcer, diabetic ulcer, or decubitus ulcer.

In one embodiment, the immunoassay of the present invention includes the steps of: a) separating proteins and fragments thereof of the fluid sample; b) reacting said separated proteins and fragments thereof with a first antibody specifically binding human fibronectin or fragments thereof; c) treating the reacted separated proteins and fragments thereof with a labeled second antibody having specific binding affinity for said first antibody; and d) determining the presence of cell adhesion-related proteins or fragments thereof by observation of label on said second antibody. The label of the second antibody is preferably a chromophore, an enzyme (such as peroxidase) catalyzing formation of observably colored product from a substrate, a radioisotope or a fluorescent compound such as fluorescein.

The present inventive method for the diagnosis of a non-healing ulcer in a human subject may also be viewed as comprising the steps of: a) obtaining a fluid sample associated with an ulcer of said subject; b) separating proteinaceous components of said sample in a matrix according to their size; c) treating said matrix with an antibody specifically binding human fibronectin or fragments thereof; and d) imaging localization of said antibody in said matrix wherein said localization is indicative of the size distribution of human fibronectin or fragments thereof, an absence of fibronectin or a presence of fibronectin fragments being indicative of a non-healing ulcer. The antibody may be radiolabeled, fluorescently labelled or coupled to another moiety conducive to visualization.

In a further embodiment, the present inventive method for the diagnosis of a non-healing ulcer in a human subject comprises the steps of: a) obtaining a fluid sample associated with an ulcer of said subject; b) separating (preferably by electrophoresis) protein and protein fragments of said sample in a matrix according to their size; c) treating said matrix with a first antibody specifically binding human fibronectin or fragments thereof; d) incubating said matrix with a second antibody conjugated to a label, the second antibody specifically binding the first antibody; and e) imaging localization of said second antibody in said matrix wherein said localization is indicative of the size distribution of human fibronectin or fragments thereof, an absence of fibronectin or presence of fibronectin fragments being indicative of a non-healing ulcer.

In another embodiment, the present inventive method for the diagnosis of an ulcer as a non-healing ulcer in a human subject comprises the steps of: a) obtaining a fluid sample associated with the ulcer of said subject; b) separating cell adhesion-related proteins and fragments thereof present in said fluid sample, said separating being on a basis of differential molecular weights; c) identifying said separated cell adhesion-related proteins and fragments thereof through a process involving treatment with antibodies specifically binding said cell adhesion-related proteins and fragments; and d) diagnosing an ulcer as a non-healing ulcer because of an absence of cell adhesion-related protein or a presence of cell adhesion-related protein fragments. A preferred separating step involves electrophoresis, usually in a gel such as polyacrylamide, most preferably in the presence of a detergent such as sodium dodecyl sulfate. This method may be modified wherein immediately prior to step (c) the method includes the additional step of: b¹) transferring separated cell adhesion-related proteins and fragments thereof to nitrocellulose paper; and step c) is modified to comprise the steps of: c¹) reacting said transferred cell adhesion-related proteins and fragments thereof with a first antibody specifically binding said cell adhesion related proteins and fragments thereof; and c²) incubating said reacted transferred proteins with a second antibody specifically binding said first antibody, said second antibody being conjugated to an enzyme such as peroxidase which forms a stain on contact with a chromophoric substrate of said enzyme.

The cell adhesion-related protein fragments which are indicative of the presence of a non-healing ulcer comprise at least one protein fragment having a molecular weight of about 125 kDa, 93 kDa, 116.5 kDa, 97 kDa, 66 kDa, or 43 kDa, most preferably 125 kDa or 93 kDa.

DESCRIPTION OF PREFERRED EMBODIMENTS

Figure 1A:
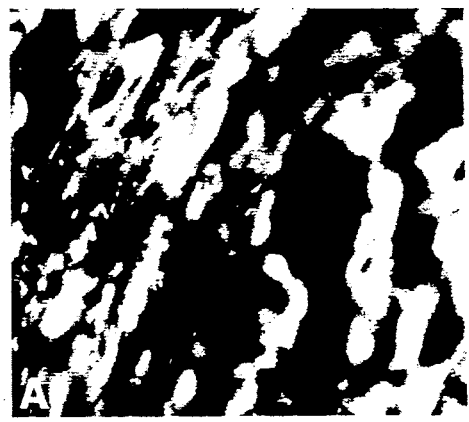
FIG. 1 shows fibronectin in punch biopsy specimens. Frozen sections were prepared from 3 mm punch biopsies and stained with polyclonal anti-human fibronectin antibodies (A,B) or non-immune IgG (C,D). A,C: fluorescence; B,D: phase contrast. Fibronectin occurred in diffuse deposits and fibrillar arrays in the wound bed. Comparison of the fluorescence and phase contrast images indicated association of fibronectin all along extracellular matrix components. With non-immune IgG, there was no staining of the sections.

The present invention relates generally to methods for the diagnosis of non-healing ulcers. These methods provide for diagnosing non-healing ulcers by assaying certain cell adhesion-related proteins or their degradation products in ulcer exudate (fluid) or tissue. The methods of the present invention provide a useful screening process for the clinical diagnosis of non-healing ulcers. The instant invention is useful in diagnosing all non-healing cutaneous ulcers, regardless of the pathology to which the ulcer is secondary. However, it is believed that the invention will be most useful in diagnosing non-healing decubitus, diabetic, and venous stasis ulcers. For purposes of the present invention a non-healing ulcer is defined as an ulcer refractory to treatment and which, if left untreated, would not heal and would persist for greater than 1 year, or an ulcer which is not progressing toward healing at a rate of at least 1 mm per week. Some examples of these treatments are: Unna boots, hydrotherapy, helium-neon laser therapy, sulitans (Travase) used in combination with silver sulfadiazine, homografts, wet-to-dry dressings, ultraviolet therapy, foam mattresses, pressure dressings (TED Hose), hydrocolloid dressings (Duoderm).

The inventive method is related to the discovery that certain proteases appeared to be present in the ulcers of patients suffering from non-healing ulcers. These proteases degraded cell adhesion-related proteins, e.g., fibronectin and vitronectin. Tests of the present invention have demonstrated that when these intact cell adhesion-related proteins are not present in the ulcer exudate or tissue, a non-healing ulcer is indicated.

According to one embodiment of the present invention, a tissue sample is obtained from a cutaneous ulcer of a human subject. For purposes of the present invention the ulcer or wound may be secondary to any pathology. However, according to one preferred embodiment, the ulcer is selected from the group consisting of decubitus ulcers, venous stasis ulcers, and diabetic ulcers. The tissue sample may be obtained by any method known in the art. According to one embodiment of the present invention, the tissue sample was obtained by punch biopsy.

The tissue sample is immunologically assayed (immuno-assayed) for a cell adhesion-related protein. The cell adhesion-related protein is most typically fibronectin or vitronectin. Fibronectin is a glycoprotein that functions as a biological adhesive and mediates bonding between a variety of cell types in their extracellular matrices. Recent studies have shown that in some cases topical application of fibronectin is an effective therapeutic approach for resolving chronic non-healing ulcers.

A preferred immunoassay of the present invention utilizes the reactivity of monoclonal or polyclonal antibodies specifically binding human fibronectin or vitronectin. Most preferably, the antibody is from a polyclonal source although monoclonal antibodies are quite usable. Tests have determined that polyclonal rabbit anti-human anti-fibronectin was sufficiently selective to be utilized in the practice of the present invention.

In one embodiment, an immunohistochemical technique may be used to determine the presence of the cell adhesion-related protein in the ulcer-associated fluid. According to one preferred embodiment, the immunoassay is preformed using an antibody which is conjugated to a fluorescent compound. Although numerous fluorescent compounds known in the art of immunohistochemistry may be utilized in the practice of the present invention, the most preferred fluorescent compounds are fluorescein and rhodamine. The tissue sample is treated with the conjugated antibody. The antibody, in turn, binds to the cell adhesion-related proteins or fragments thereof, making them observable. Thus, the relative amount of observable fluorescence of the sample is indicative of the presence of the cell adhesion-related protein. Further, cell adhesion-related proteins can be quantitatively and qualitatively assayed using the inventive method. Tests of the present invention indicate that an observable fluorescence associated with intact fibronectin or vitronectin which is notably less than that of a control sample obtained from a healthy individual indicates the presence of a non-healing ulcer.

According to a further embodiment, the tissue sample is reacted with a first antibody which specifically binds a cell adhesion-related protein. The tissue sample is subsequently reacted with a second antibody which specifically binds the first antibody. The second antibody is preferably conjugated to a label such as a fluorescent compound, or more preferably, an enzyme such as peroxidase. The enzyme forms a visibly colored precipitate on contact with an appropriate chromophoric substrate. Thus, the antibody-reacted tissue sample is treated with enzyme substrate and an observable product forms. Therefore, the presence of the cell adhesion-related protein may be determined through immunoassay fluorescence observation or enzymatic assay (ELISA) techniques. The above techniques produce an observable change in the specimen which may be used clinically to determine the presence of a cell adhesion-related proteins or fragments thereof.

A further aspect of the present invention is directed to assaying a sample (preferably a fluid sample) collected from the ulcer of a subject to more generically isolate or identify cell adhesion-related proteins and their degradation products therein. For example, degradation products from fibronectin, are protein fragments having molecular weights of about 125 kDa, 93 kDa, 200 kDa, 116.5 kDa, 97 kDa, 66 kDa, and 43 kDa, the first two of which are preferred. Tests of the present invention have shown that the identification of at least one of these degradation products in the sample indicates a non-healing ulcer. Further tests of the present invention have demonstrated that electrophoresis, alone or, more preferably, in combination with cell-blotting or immunoassay techniques, may be used to isolate and/or identify these degradation products, as well as the cell adhesion-related proteins themselves.

According to a preferred embodiment, a sample is obtained from the ulcer of the subject. Most preferably, the sample is fluid exudate from the ulcer. The proteins included in the sample are thereafter separated according to their molecular weight. The most preferred method for separating the proteins is electrophoresis. Suitable electrophoresis procedures are known in the art, and any electrophoresis method which effectively separates proteins having a molecular weight of from about 20 to about 1000 kDa may be used in the practice of the present invention. According to one test of the present invention, the samples were electrophoresed using the SDS-PAGE method. The samples for electrophoresis were dissolved in reducing sample buffer (62.5 mM Tris-HCl, 2% lauryl sulfate, 10% glycerol, 0.01% bromphenol blue, 5% mercaptoethanol, pH 6.8), boiled for three minutes and electrophoresed using a 4-16% acrylamide slab gel containing a gradient of 3M to 8M urea and a discontinuous buffer system (0.025M Tris-HCl, 0.129 glycine, 0.1% lauryl sulfate). The electrophoretic gels were prepared using N-N'-methylenebisacrylamide as a crosslinker. In general, each lane was loaded with about 150 micrograms of protein from the sample. After electrophoresis the gels were incubated for one hour in 50% trichloroacetic acid to precipitate the proteins. The precipitated proteins were thereafter stained with Coomassie Brilliant Blue R-250 (Sigma Chemical, St. Louis, Mo). The above method was repeated using samples from healthy volunteers in order to develop controls.

The stained separated proteins appeared as colored bands in the electrophoretic gels, each band corresponding to a protein or peptide having a particular molecular weight. By comparing the sample taken from the subject to that from the controls, particular fibronectin fragments were identified in one embodiment. Specifically, tests of the present invention have isolated and identified fragments having molecular weights of about 125, 93, 116.5, 97, 59, 53, 42, 28 and 25 kDa. Further tests of the present invention have determined that the presence of at least one protein fragment having a molecular weight of about 125, 93, 116.5 97, 59, 53, 42, 28, or 25 kDa in a sample is indicative of the presence of non-healing ulcers. Further, it has been determined that samples obtained from the non-healing ulcers of patients lacked any intact cell adhesion-related proteins, e.g., fibronectin. Therefore, it is believed that the above protein fragments which have been identified as appearing in non-healing ulcer samples are, in fact, degradation products of a cell adhesion-related protein. In a further test of the present invention, it was demonstrated that fibronectin, when added to samples collected from non-healing ulcers, was degraded into protein fragments having molecular weights of about 125, 93, 116.5, 97, 59, 53, 42, 28, and 25 kDa. Accordingly, it appears that the non-healing ulcer includes proteases which degrade cell adhesion proteins into the protein components identified above. The effect of this protease and possibly the presence of the degradation products themselves (particularly the 125 kDa and 93 kDa fragments), appears to inhibit ulcer healing.

A most preferred aspect of the present invention provides a method which uses electrophoresis in combination with immunoassay to isolate and identify the cell adhesion-related proteins and their degradation products. According to one embodiment, a sample is obtained from the ulcer of the subject. The peptides and proteins included in the sample are then electrophoretically separated according to their molecular weights. Once separated, the peptides and proteins are transferred onto a nitrocellulose paper substrate. Techniques for transferring separated proteins from an electrophoretic gel onto a another substrate are well know in the art. Preferably, a western blot technique and analysis is used in the practice of this embodiment of the present invention. The separated proteins are then reacted with a first antibody which specifically binds a cell adhesion-related protein and at least some of its degradation products. The first antibody was a polyclonal anti-fibronectin antibody obtained from immunized rabbits by the method of Grinnell and Feld, Cell 17, 117-129 (1979) which is incorporated by reference herein. The separated proteins are subsequently reacted with a second antibody which specifically binds with the first antibody. The second antibody, as discussed above, is preferably conjugated to a fluorescent compound or an enzyme which forms a stain on contact with a particular substrate of said enzyme. If the second antibody is conjugated to peroxidase, the separated proteins are stained by treating the proteins with a chromophore-forming peroxidase substrate. The stained separated proteins appear as individual bands of stain. The relative position of a particular band of stain is indicative of the presence of a protein having a specific molecular weight. The presence of particular bands of stain correspond to the cell adhesion-related proteins and their degradation products, and accordingly, are indicative of the presence of a non-healing ulcer.

In the present study, acute and chronic wound fluids were analyzed by immunoblotting with polyclonal and monoclonal antibodies to characterize specific fibronectin and/or vitronectin fragments; by cell blotting to identify biologically active fragments (Hayman et al., 1982, J. Cell Biol. 95:20-23); and by cell attachment to determine if chronic wound fluid contained inhibitors of adhesion. Vitronectin in acute and chronic wound fluid was also studied. Vitronectin is a second major cell-adhesion protein found in blood (Preissner, 1989, Blut 59:419-431) and also increases in some tissues during inflammation (Reilly et al., 1988, J. Clin. Pathol. 41:1269-1272). The present results show that in wound fluid from some venous stasis ulcers, proteolysis resulted in complete degradation of intact fibronectin and vitronectin and the appearance of biologically active fibronectin fragments containing the arg-gly-asp (RGD) cell binding domain. Wound fluid lacking intact fibronectin and vitronetin, probably as a result of protease activity, inhibited cell attachment to gelatin and fibronectin.

In these studies, immunoblotting with polyclonal and monoclonal antibodies was used to identify fibronectin, vitronectin, and fibronectin degradation products, and, by cell blotting, general cell-adhesion proteins identified. Fibronectin and vitronectin are two major adhesion protein systems in blood (Mosher, 1989, *Fibronectin*, Academic Press Inc. San Diego; Preissner, 1989, Blut 59:419,431), but the adhesion protein systems in wound fluid have not been previously characterized.

The profiles of fibronectin and vitronectin in suction blister fluid and mastectomy fluid were similar to those observed in serum and plasma. Under reducing conditions, fibronectin appeared primarily as a 250 kDa subunit that migrated at 440 kDa under non-reducing conditions. Vitronectin appeared as a doublet around 60 kDa, which is lower than the expected 65 and 75 kDa polypeptides, but the vitronectin bands appeared to be compressed beneath the large albumin band.

Adhesion proteins detected by cell blotting included those corresponding to the fibronectin and vitronectin bands stained by immunoblotting. SEM observations confirmed that eukaryotic cells were attached and slightly spread on the nitrocellulose paper. The method for cell blotting used in these studies was very sensitive. Eukaryotic cells having affinity for cell adhesion proteins were cultured on the nitrocellulose paper solid matrix in a eukaryotic cell culture medium. Cell attachment occurred at those places on the solid matrix comprising cell adhesion proteins or cell adhesion protein fragments with cell adhesion binding activity. A variety of eukaryotic cells may be utilized for these purposes and such varieties are well known to those of skill in the art. These include BHK cells, NRK cells, melanoma cells or rat calvaria bone cells. Ferro et al., Biochem. Soc. Tr. 16:144-146 (1988) showed melanoma cell attachment to cell adhesion protein matrices. Wong et al., Biochem. J. 232:119-123 (1985) showed the rat calvaria bone cell attachment to cell adhesion protein solid matrices. Hayman et al., J. Cell Biol. 95:20-23 (1982) showed attachment of normal rat kidney (NRK) to cell adhesion proteins on the solid matrix.

It should be noted that a kit useful for the diagnosis of non-healing cutaneous ulcers is readily producible in view of the invention described herein. Such a kit would of course include a carrier compartmentalized to receive one or more container means in close confinement therein. A first container means would include an antibody having binding affinity for fibronectin or vitronectin. Additionally, at least one of a second container means comprising a preformed electrophoretic gel and a third container means comprising a fibronectin or vitronectin electrophoretic standard would be utilized. Such a kit could be readily adapted for the detection of cell adhesion protein fragments or the absence of cell adhesion protein fragments and samples from cutaneous ulcers.

Of course many other means of detecting cell adhesion proteins or their fragments are known to those of skill in the art. Such means may, for example, take advantage of the affinity of cells as described above for cell adhesion proteins. The facilitation of cell binding by cutaneous ulcer associated fluids or the inhibition of binding to preformed cell adhesion protein-coated matrices by such fluids could, of course, both be used for such purposes.

The 40 kDa polypeptide in certain samples that stained with anti-vitronectin antibodies is probably a vitronectin fragment (Conlan et al., 1988, Blood, 72:185-190). The higher molecular mass >250 kDa group of adhesion-promoting polypeptides also stained with anti-fibronectin antibodies if the blots were overdeveloped (see Example 1 and Wysocki et al, 1990, Lab. Invest. 63:825-831). These polypeptides, which were much more prominent in serum and blister fluid than in plasma, are likely to be covalently-crosslinked fibronectin complexes.

The biological activity of the adhesion-promoting polypeptides appeared to depend on the RGD recognition mechanism. The peptide GRGDSP but not GRGESP completely inhibited attachment to vitronectin and the 40 kDa vitronectin fragment. GRGDSP also substantially reduced attachment and inhibited spreading on fibronectin and >250 kDa polypeptides.

Chronic wound fluid was markedly different from acute wound fluid such as suction blister fluid or mastectomy fluid. Type A chronic wound fluid, observed with 3/11 patients, was characterized by complete degradation of vitronectin and fragmentation of fibronectin into small molecular mass polypeptides ranging up to 125 kDa in size. Three of these polypeptides (54, 93, and 125 kDa) had cell attachment activity and were recognized by monoclonal antibodies that bind fibronectin near the RGD domain. The biological activity of these fragments was inhibited by GRGDSP.

Type B chronic wound fluid, observed with 8/11 patients, was characterized by partial degradation of fibronectin resulting in a mixture of intact subunits and fragments. Unlike fibronectin in plasma or suction blister fluid, fibronectin in type B chronic wound fluid was unable to form normal dimers. This indicates that the fibronectin subunits might have lost a portion of the carboxy terminal domain, which is known to be protease sensitive (Chen et al., 1966, Biochim. Biophys. Acta 493:310-322).

Fibronectin in chronic wound fluid gave a strong signal when stained with monoclonal antibodies directed against cellular fibronectin (Borsi et al., 1987, J. Cell Biol. 104:595-600). This indicates that at least part of the fibronectin in wound fluid is derived locally from cells in the wound bed. Previous immunofluorescence (Clark et al., 1983, J. Invest. Dermatol. 80:26s-30s) and in situ hybridization studies (French-Constant et al. 1989, J. Cell Biol. 109:903-113) showed that cellular fibronectin was present in experimental wounds. Apparently, the cells in chronic wounds retain the ability to synthesize and secrete fibronectin, and probably other extracellular matrix proteins.

Attachment assays with type A and type B chronic wound fluids demonstrated that these differed in their biological activities. Type B wound fluid, which contained partially intact fibronectin and vitronectin, promoted cell attachment to gelatin. Type A wound fluid, on the other hand, was unable to promote cell attachment to gelatin and inhibited cell attachment to serum-coated gelatin. Type A wound fluid also caused reversible rounding of cells previously spread on fibronectin. The effects of type A wound fluid were neutralized by excess fetal bovine serum (which contains protease inhibitors) but not by excess fibronectin. These results indicate that presence of protease activity in type A wound fluid (see Example 1 and Wysocki et al., 1990, Lan Invest., 63:825-831) rather than the absence of intact adhesion proteins may be responsible for inhibition of cell adhesion.

Elevated protease activity in the wound be could explain impaired keratinocyte migration and failed closure of some chronic ulcers. Moreover, fibronectin fragments may help maintain high protease levels by stimulating neutrophil degranulation (Wachtfogel et al., 1988, J. Clin. Invest. 81:1310-1316) and fibroblast secretion of metalloproteases (Werb et al., 1989, J. Cell Biol. 109:877). Also, some fibronectin fragments exhibit endogenous protease activity towards gelatin and laminin (Planchenault et al., 1990, Biol. Chem. Hoppe-Seyler 371:117-128).

Little has been published about proteases in the wound matrix. Collagenase and elastase have been detected in blister fluid from bullous skin diseases (Oikarinen et al, 1983, J. Invest. Dermatol. 81:261-266) and corneal ulcers contain increased levels of plasminogen activator (Berman et al. 1983, Invest. Ophthalmol. Vis. Scil 24:1358-1366). Elevation of proteases in wound fluid could interfere with normal healing not only by degrading adhesion proteins, but also, by degrading other factors necessary for repair. Many of these factors can be found in wound fluid, e.g., TGF-$\beta$ (Cromack et al., 1987, J. Surg. Res., 42:622-628), EGF (Grotendorst, et al., 1989, J. Cell Physiol., 139:617-623), and several cytokines (Ford et al, 1989, Arch. Surg. 124:1422-1428). Growth-regulating factors have been detected in human wound fluid that accumulated beneath an occlusive wound dressing (Alper et al., 1985, J. Invest. Dermatol., 84:513-515), and PDGF-related peptides were found in mastectomy fluid (Matsuoka et al. 1989, Proc. Natl. Acad. Sci. USA, 86:4416-4420).

Increased levels of proteolytic enzymes in chronic wounds may be of considerable importance not only to understanding the etiology of defective wound closure, but also, to planning appropriate therapeutic intervention. Responses of patients with chronic stasis ulcers to therapy with crude preparations such as platelet releasate (Knighton, et al., 1986, Ann. Surg. 204:322-330; Knighton et al., 1990, Surg. Gyn. Obst. 170:56-60) or purified proteins such as fibronectin (Wysocki et al., 1988, Arch. Dermatol., 124:175-177) may vary considerably depending upon the level of proteolysis occurred in the wound bed.

Having now described the invention, the same will become better understood by reference to certain specific examples, which are included for the purposes of explanation only and are not intended to be limiting unless otherwise specified.

EXAMPLE 1

Specimens for immunofluorescence

Tissue sections were prepared from 3 mm punch biopsy specimens obtained from subjects who were enrolled in a fibronectin leg ulcer study. The subjects had been previous treatment failures with therapies such as Unna boots, gradient compression stockings and wet to dry dressings. Following punch biopsy, specimens were immediately placed in Tissue-Tek O.C.T. compound (Miles Laboratories) being careful to maintain proper orientation and frozen in liquid nitrogen. Primary antibodies were a polyclonal rabbit anti-human fibronectin antibodies prepared for these purposes. Sections were rinsed with phosphate saline (PS) containing 1% bovine serum albumin (BSA) and 1% glycerine and then treated for 30 min at 37° C. with primary antibody diluted with PS. Goat anti-rabbit IgG was used for controls. The sections Were rinsed 3×10 min with PS and then treated for 30 min at 37° C. with the appropriate fluorescein conjugated second antibody. Sections were then rinsed as above and mounted with 0.1% phenylenediamine, 90% glycerol, pH 8.0. Observations were made with a Zeiss photomicroscope.

Collection and preparation of wound fluid

Fluid was obtained from surgical mastectomy wounds, chronic venous leg ulcers (exudate), and suction blisters. Ages of male and female subjects ranged from 24 to 65 years of age. Subjects with mastectomy and chronic wounds were recruited from in-patient and out-patient populations of a large metropolitan hospital. Suction blister fluid was obtained from normal volunteers. Mastectomy fluid was collected from fluid collection devices (HemoVac and ConstaVac) in sterile test tubes (Corning) beginning 24 hours after surgery and then every day until drains were removed (up to nine days). Mastectomy patients all had tumors with well defined margins. Fluid collection periods began after emptying and lasted about four hours. Fluid from chronic non-healing ulcers, those present for 1 year or not progressing towards healing at a rate of at least about 1 mm per week, was collected from beneath a transparent polyurethane occlusive dressing (Tegaderm, 3M, St. Paul, Minn.) placed over the wound for 4 to 12 hours using a sterile tuberculin syringe equipped with a 20-gauge stainless steel needle, being careful to avoid injury to the underlying granulation tissue. Blister fluid was collected as above from suction blisters made on the forearm of normal volunteers using a suction blister device (Dermovac, Mediko Medical, Espoo, Finland). After collection all fluids were immediately placed on ice and carried to the laboratory where they were centrifuged (Microfuge II, Beckman) for 4 min at $11,600 \times g$ in sterile 1.5 ml centrifuge tubes and the pellet discarded. The supernatant was sterilely pipetted into sterile 1.5 ml centrifuge tubes and frozen at $-70°$ C. until needed.

Collection of blood and preparation of blood derived serum (BDS) and plasma derived serum (PDS)

Blood samples were collected in sterile blood sampling tubes containing 10.5 mg EDTA, 0.014 mg potassium sorbate in 0.07 ml of 15% EDTA (Vacutainer, Becton Dickinson, Rutherford, N.J.) from the antecubital vein of subjects with chronic wounds and suction blisters using a 21 gauge stainless steel needle attached to a blood collection device (Vacutainer, Becton Dickinson, Rutherford, N.J.). To prepare blood derived serum (BDS), 1 M $CaCl_2$ was added to the blood sampling tube to result in a final concentration of 14 mM. This tube was then incubated for 2 hours at 37° C. Following incubation, the serum was removed and the sample was centrifuged (Sorvall RC2-B, SS34 rotor) at $1,800 \times g$ for 15 min at 37° C. The resulting supernatant was removed and recentrifuged at $22,000 \times g$ 30 min at 37° C. Next the BDS was dialyzed in Dulbecco's phosphate buffered saline (DPBS, 150 mM NaCl, 3 mM KCl, 6 mM $Na_2HPO_4.7H_2O$, 1 mM $KH_2PO_4$, 1 mM $CaCl_2.H_2O$, 0.5 mM $MgCl_2.H_2O$, pH 7.2) at 4° C. overnight, using at least $100 \times$ the BDS volume. After dialysis, the BDS was again centrifuged at $22,000 \times g$ for 30 min at 37° C., filter sterilized using a 0.2 µm filter (Millipore GV, Bedford, Mass.), placed in sterile 1.5 ml centrifuge tubes and stored at $-70°$ C. until needed. Plasma-derived serum was prepared by first centrifuging at $1,800 \times g$ for 15 min at 4° C. The resulting plasma was removed and centrifuging at $22,000 \times g$ for 30 min at 4° C. The plasma was again removed and 1M $CaCl_2$ was added to a final concentration of 20 mM and then incubated for 2 hours at 37° C. After incubation the sample was centrifuged at $22,000 \times g$ for 30 min at 37° C. and then dialyzed, centrifuged, filtered and stored as described above.

Protein determination. SDS-PAGE, and Western blotting

Protein determination of all wound fluid, BDS, and PDS samples was done using a modified Lowry method. Briefly, after adding the sample (100 µl), diluted if necessary, to test tubes, distilled deionized water (DDW) was added to a total volume of 1.0 ml. After adding 0.5 ml of 1 N NaOH, samples were vortexed. Next, 2.0 ml of Lowry solution (solution A=2% $Na_2CO_3$ in 0.1N NaOH; solution $B_1$=1% $CuSO_4.5H_2O$; and solution $B_2$=2% K(Na) tartrate—in a proportion of 10:0.1:0.1 respectively) was added and the samples were vortexed and incubated for 10 min at room temperature (R.T.). Lastly, 0.5 ml of a dilute phenol solution (Sigma, St. Louis, Mo.), 1.0 ml of phenol:1.0 ml of DDW, was added and the samples were vortexed immediately after addition to each tube and incubated for 30 min at R.T. Optical density determinations ($OD_{640}$) were made using a spectrophotometer (DU-40 Spectrophotometer, Beckman) from which protein concentrations were calculated.

Samples for electrophoresis were dissolved in reducing sample buffer (62.5 mM Tris-HCl, 2% lauryl sulfate, 10% glycerol, 0.01% bromphenol blue, 5% mercaptoethanol, pH 6.8), boiled for 3 min and electrophoresed using a 4 to 16% acrylamide gradient slab gel containing a gradient of 3M to 8M urea and a discontinuous buffer system (0.025M Tris-HCl, 0.192 glycine, 0.1% lauryl sulfate). Gels were prepared using N-N'-methylene-bis-acrylamide as the crosslinker. In general each lane was loaded with ~150 µg of protein from wound fluid, BDS, and PDS samples. After electrophoresis, gels were either incubated for 1 hour in 50% trichloroacetic acid (TCA) to precipitate the proteins and then stained with Coomassie Brilliant Blue R-250 (Sigma Chemical, St. Louis, Mo.) or used for Western blotting.

For Western blotting, gels were removed from between the glass plates and placed in a holder such that the gel was between a piece of nitrocellulose paper (NC), 0.45 µm (Schleicher & Schuell, Keene, N.H.) and filter paper (Whatman #3 mmChr, Maidstone, England) accompanied by sponges on either side. The sandwich holder was then placed in a transfer tank (Hoefer TE-50, San Francisco, Calif.) containing transfer buffer (10 mM Tris-HCl, 75 mM glycine, 10% methanol) so that the nitrocellulose paper was between the gel and anode. Transfer was accomplished by electrophoresin for 1.5 hours at 150 mA followed by 1.5 hours at 300 mA at 4° C. Immunoblotting of the protein laden nitrocellulose paper was done by drying the nitrocellulose paper for 30 min at 37° C. Following this, the paper was blocked for 1 hour at room temperature using a 3% gelatin-tris buffered saline solution (TBS), 20 mM Tris-HCl, 500 mM NaCl, pH 7.5. After blocking, the NC paper was washed for 5 min $\times$ 2 with a polyoxyethylene sorbitan monolaureate (Tween-20, BioRad, Richmond, Calif.) TBS solution (0.05% Tween-20, pH 7.5). Next the blot was incubated with a polyclonal anti-FN antibody for 2 hours at room temperature using a peroxidase-conjugated goat anti-rabbit IgG (Boehringer Mannheim, Indianapolis, Ind.) antibody. After washing twice for 5 minutes as described previously and then washing once for 5 minutes with TBS the proteins were visualized using diaminobenzidine (DAB), 0.5 mg/ml TBS, to which is added immediately before addition to the blot, 1 µl of 30% $H_2O_2$ for every 1 ml of DAB/TBS.

Incubation of chronic wound fluid

Chronic wound fluid samples were incubated with FN, 0.2 µg FN/150 µg wound fluid protein for 0, 15, and 60 min in a humidified incubator at 37° C. At the end of each incubation period, samples were added to reducing buffer, boiled for three minutes, electrophoresed and stained or blotted.

To determine the amount of FN to add to the chronic wound fluid samples, 150 µg of protein form samples of mastectomy fluid, suction blister fluid, BDS and PDS, along with known concentrations of FN ranging from 0.125 to 2.0 µg were loaded onto an SDS-PAGE gel and Western blotted as already described. After Western blotting the nitrocellulose paper was scanned using a laser densitometer (Ultrascan XL, LKB, Bromma, Sweden) interfaced to a line printer. From the output a graph was constructed for the known amounts of fibronectin (FN). This graph was then used to estimate the amount of FN/150 µg of protein found in the wound fluids and serum samples.

Fibronectin in punch biopsy specimens

Figure 1B:
Figure 1C:
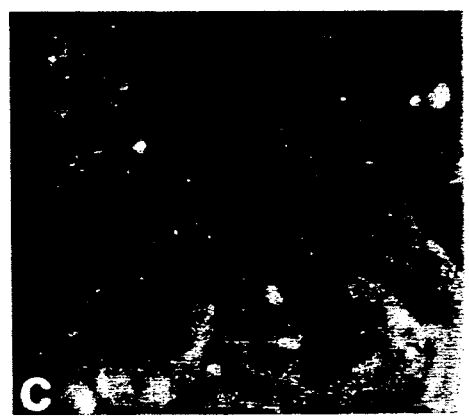
Figure 1D:
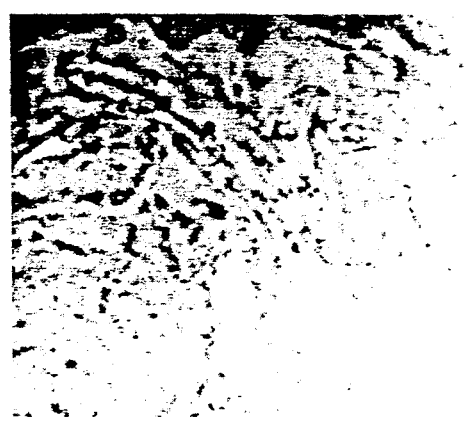

To determine if poor epithelization of venous stasis ulcers might be explained by the absence of fibronectin in the wound bed, frozen sections of 3 mm punch biopsies were prepared and stained with polyclonal anti-FN antibodies. FIG. 1A shows that there was extensive fibronectin antigen in diffuse deposits and fibrillar arrays in the wound bed. Comparison of the fluorescence and phase contrast images (FIGS. 1A and 1B) indicated association of fibronectin with other extracellular matrix components, similar to the distribution of fibronectin in normal granulation tissue. Control sections incubated with rabbit IgG showed no staining (FIGS. 1C, 1D).

Comparison of chronic non-healing ulcer and blister wound fluid

The above result indicated the presence of fibronectin antigen in the wound bed. Because a polyclonal antibody was used, indirect immunofluorescence would not distinguish intact from partly degraded fibronectin. To make this distinction, samples of wound fluid were obtained and analyzed by SDS-PAGE and by immunoblotting with polyclonal anti-FN antibodies.

Figures 2A, 2B:
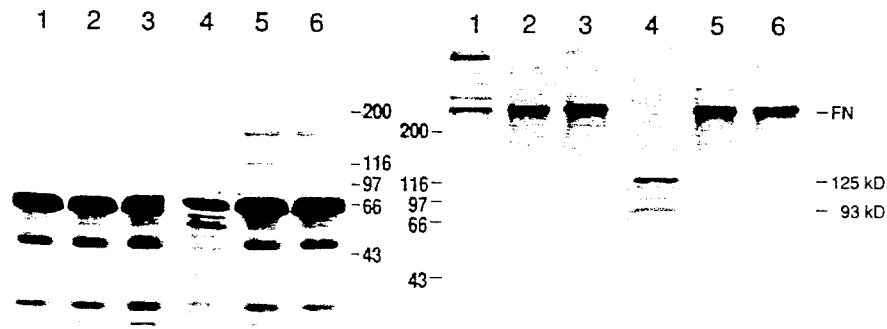
FIG. 2 shows fibronectin in chronic wound fluid. SDS-PAGE analysis showed protein (Coomassie Blue) (panel A) and fibronectin (immunoblotting) (panel B) profiles. Samples in lanes 1-3 respectively are suction blister fluid, blood derived serum (BDS), and plasma derived serum (PDS) from a normal volunteer. Samples in lanes 4-6 respectively are chronic wound fluid, BDS, and PDS from a patient with a venous stasis ulcer. The BDS and PDS protein profiles appeared identical, and fibronectin in serum was primarily a single band ~250 kDa. In marked contrast, high molecular weight proteins were mostly absent from chronic wound fluid. The ~250 kDa fibronectin subunit was absent, and only fibronectin fragments were detected. The major fragments were about 125 and 93 kDa. In comparison, there was no degradation of fibronectin in suction blister fluid, but some high molecular weight fibronectin-containing components were detected. Each lane contained 150 μg protein.

FIG. 2 shows the protein (panel A) and fibronectin (panel B) profiles of chronic wound fluid (lane 4) compared to serum samples from the same patient (lanes 5 and 6). For each patient, wound fluid was compared to serum to make it possible to distinguish local (wound fluid) from systemic (serum) changes in fibronectin. In case there were systemic changes, serum samples were prepared both from blood that contained cells (blood-derived serum, BDS) and from blood with cells removed (plasma-derived serum, PDS).

In BDS and PDS, there were essentially identical protein profiles (FIG. 2, A5 and A6). Fibronectin was most intact with the subunits migrating in a single band at ~250 kDa (B5). In wound fluid from venous stasis ulcers, high molecular weight components stained by Coomassie Blue were decreased compared to serum (A4). The ~250 kDa fibronectin subunit detected by immunoblotting was absent. Only fibronectin fragments were evident (B4). The major fragments were about 125 and 93 kDa.

The above result showed that fibronectin in chronic stasis ulcer wound fluid was degraded. Degradation occurred locally in the wound bed, not systemically in blood. To learn if fibronectin degradation was specific for venous stasis ulcers, the condition of fibronectin in other types of wounds was studied.

FIG. 2 shows that there was no degradation of fibronectin in suction blister fluid (B1). The intact fibronectin subunit had the same molecular mass in suction blister fluid (250 kDa) as in serum (B2 and B3). Also, the protein profile of suction blister fluid (A1) appeared identical to serum (A2 and A3). The presence of intact fibronectin in normal cutaneous wound fluid suggests that fibronectin degradation is not a feature of normal healing.

Interestingly, there were some high molecular weight fibronectin-containing components in suction blister fluid (B1). This was more evident in the blister fluid than in corresponding serum samples B2 and B3. These high molecular weight components appear to be covalently crosslinked (by other than disulfide linkages) since they were not disaggregated by the combination of SDS and reducing agent. Fibronectin can covalently crosslink to itself and to fibrin.

Examination of mastectomy wound fluid

Figures 3A, 3B:
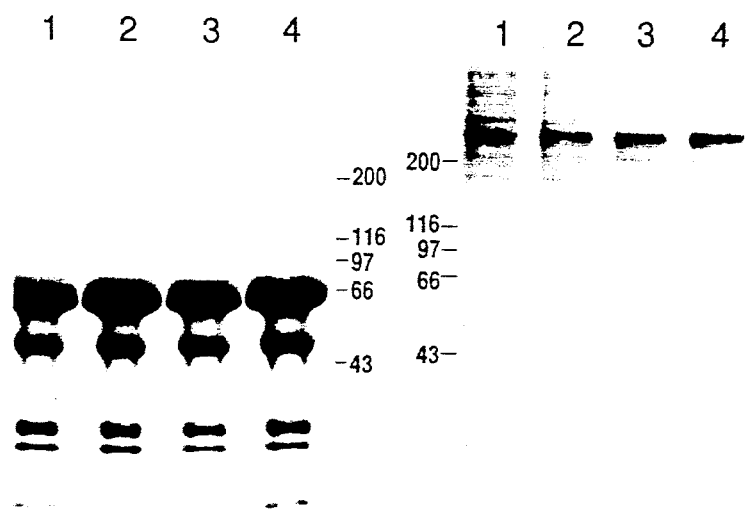
FIG. 3 shows fibronectin in mastectomy wound fluid. SDS-PAGE analysis showed protein (panel A) and fibronectin (panel B) profiles for mastectomy fluid. The samples were obtained 1 day (lane 1), 2 days (lane 2), 3 days (lane 3) and 5 days (lane 4) after surgery. The protein profiles were similar to each other. There was no degradation of fibronectin, and the ~250 kDa subunit was prominent. In the early mastectomy fluid samples, day 1 and day 2, there were high molecular weight fibronectin-containing components.

The protein and fibronectin profiles in wound fluid from surgical (mastectomy) wounds were also studied. FIG. 3 shows the protein (panel A) and fibronectin (panel B) profiles in mastectomy fluid collected on days 1, 2, 3, and 5 after surgery (lanes 1, 2, 3, and 4). The protein profiles were similar to each other and to suction blister wound fluid (FIG. 2). There was no degradation of fibronectin, and the ~250 kDa subunit was prominent. In the early mastectomy fluid samples, days 1 and 2, there were high molecular weight fibronectin-containing components. Mastectomy fluid collected 9 days after surgery appeared identical to that collected 5 days after surgery. These results support further the idea that fibronectin in wound fluid normally is intact.

Further examination of chronic non-healing ulcer fluids

Figure 4:
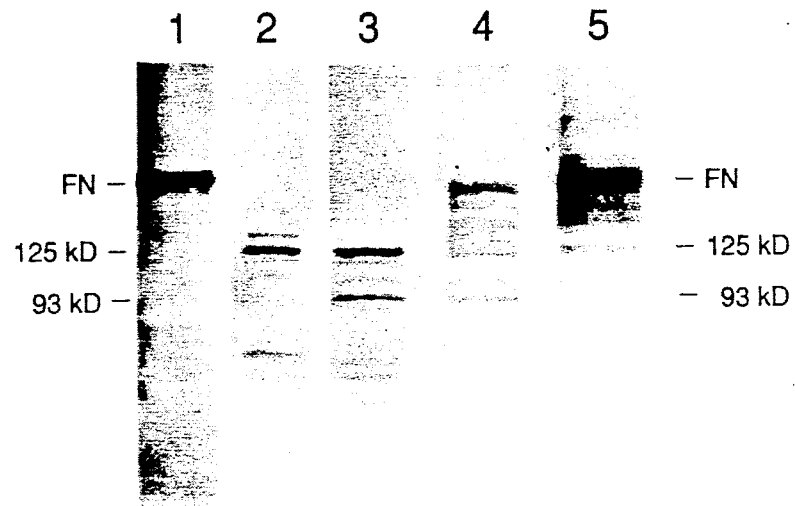
FIG. 4 shows a comparison of fibronectin profiles in chronic wound fluid from different patients. Lane 1: human plasma fibronectin (0.2 μg). Lanes 2 and 3: chronic wound fluid samples from two patients with venous stasis ulcers. Lanes 4 and 5: chronic wound fluid from two patients with non-insulin dependent diabetes. Less degradation of FN was observed in the wound fluid of patients with non-insulin dependent diabetes. Common to all of the fibronectin degradation profiles was the 125 kDa fragment. Otherwise, the profiles were similar but not identical. Each wound fluid lane contained 150 μg protein.

To learn if fibronectin degradation was typical of chronic leg ulcers or unique to the first patient whose wound fluid was analyzed, several other patients were recruited to the study. One of these patients showed extensive fibronectin degradation in the wound fluid (FIG. 4, lane 3) similar to the first patient in the study (lane 2). Both of these cases were diagnosed with venous stasis ulcers. With the other two patients, there also was fibronectin degradation but to a lesser extent (lanes 4 and 5). These latter two cases were both non-insulin dependent diabetics. In general, fibronectin degradation profiles were similar but not identical. Only the 125 kDa fragment was common to all four wound fluid samples.

Incubation of fibronectin with chronic non-healing ulcer fluid

Figure 5:
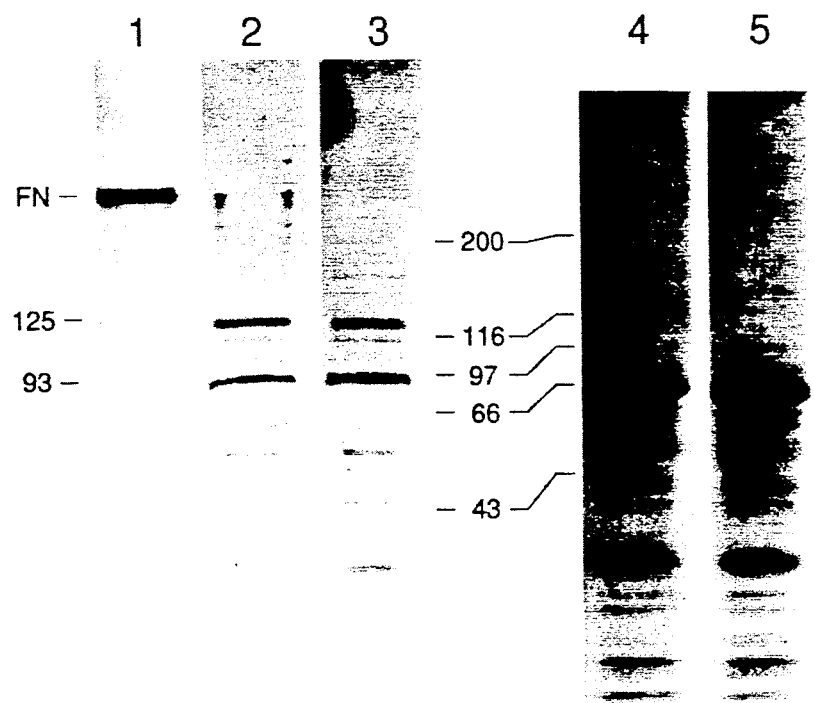
FIG. 5 shows fibronectin-degrading protease activity in chronic wound fluid. Plasma fibronectin (0.2 μg) was reconstituted with chronic wound fluid (150 μg) and incubated at 37° C. Lane 1: starting fibronectin. Lanes 2 and 4: fibronectin and protein profiles of chronic wound fluid incubated with fibronectin for ~10 sec. Lanes 3 and 5: fibronectin and protein profiles of chronic wound fluid incubated with fibronectin for 15 min. The intact fibronectin subunit was degraded immediately, and there were some fragments with molecular weights around 200 kDa. Complete degradation of the high molecular weight forms occurred by 15 min.

Because the fibronectin fragment profiles were similar, a common proteolytic activity might have been present in the chronic ulcers. As a first step towards identifying the protease(s) in the wound bed, wound fluid was tested to learn if it contained fibronectin-degrading activity. This was accomplished by mixing intact fibronectin with wound fluid and incubating the samples at 37° C. FIG. 5 shows purified plasma fibronectin (0.2 μg) immediately before (lane 1) and 10 sec after (lane 2) incubation with chronic wound fluid (150 μg protein). The intact fibronectin subunit was mostly degraded, and there were some fragments with molecular weights around 200 kDa. Complete degradation of the high molecular weight fragments occurred by 15 min (lane 3). At this time, the major components were the 125 and 93 kDa fragments already described. Over the same time, there was no change in the Coomassie Blue pattern (lanes 4 and 5). These results show directly that chronic wound fluid contains active protease(s) that can degrade fibronectin.

The purpose of the examples described above was to analyze fibronectin in chronic leg ulcers. Fibronectin was found to be extensively degraded in venous stasis ulcers and partially degraded in diabetic ulcers. Degradation was confined to the wound fluid and not systemic. Moreover, there was no degradation of fibronectin in fluid obtained from control cutaneous wounds or surgical wounds.

The identity of protease(s) responsible for degradation of fibronectin in chronic leg ulcers is unknown, but the above results show that degradative enzyme activity can be found in the wound fluid. Fibronectin is sensitive to many different proteases. These proteases include plasmin and plasminogen activator which are believed to be elevated in non-healing corneal ulcers. Nevertheless, elevated plasminogen activator may be a normal feature of cutaneous wound healing. Also, studies on the formation of decubitus ulcers, another type of non-healing ulcer, showed decreased fibrinolysis in wound fluid.

Other fibronectin-degrading proteases including collagenase and elastase, have activities elevated in blister fluid from patients with bullous diseases. Increased collagenase inhibitor activity has also been reported in bullous blister fluid. Fibronectin fragments identified in bronchoalveolar lavages from smokers have been attributed to elevated elastase activity.

EXAMPLE 2

Materials

Baby hamster kidney (BHK) cells adapted for growth in suspension culture were cultured as described previously (Grinnell et al., 1988S, J. Cell Sci., 90:201–214). Human plasma FN was obtained from the New York Blood Center, New York, N.Y. Human vitronectin was prepared from outdated human blood by heparin affinity chromatography (Yatohgo et al., 1988, Cell Struct. Func., 13:281–292). Polyclonal anti-fibronectin antibodies were prepared in our laboratory. Polyclonal anti-vitronectin antibodies were prepared in our laboratory. Polyclonal anti-vitronectin antibodies were a gift from Dr. Deanne Mosher, Department of Medicine, University of Wisconsin. Mouse monoclonal antibody against the cellular fibronectin specific ED-A domain was a gift from Dr. Luciano Zardi, National Institute for Cancer Research, Genova, Italy. Mouse monoclonal antibody against the fibronectin cell binding domain was purchased from Telios Pharmaceuticals, Inc. (San Diego, Calif.). Synthetic peptides: Gly-Arg-Gly-Glu-Ser-Pro (GRGESP) and Gly-Arg-Gly-Asp-Ser-Pro (GRGDSP) were purchased from Peninsula Laboratories (Belmont, Calif.).

Wound fluid

Patients undergoing surgical mastectomy (5 persons) or with chronic leg ulcers (11 persons) were recruited from in-patient and out-patient populations of a large, metropolitan hospital. Suction blister fluid was obtained form normal volunteers (3 persons).

Chronic leg ulcers were present for >1 year or healing at <1 mm per week. Fluid was collected from beneath a transparent polyurethane occlusive dressing (Tegaderm, 3M, St. Paul, Minn.) placed over the wounds for 4 to 12 hours. Fluid collection was accomplished using a sterile tuberculin syringe equipped with a 20 gauge stainless steel needle, being careful to avoid injury to the underlying granulation tissue. Leg ulcers showed no signs of clinical infection at the time wound fluid was obtained.

Mastectomy fluid was collected from fluid collection devices (HemoVac and ConstaVac) in sterile test tubes beginning 24 hours after surgery and then every day until the drains were removed (up to nine days). Mastectomy patients all had tumors with well defined margins. Fluid collection periods began after emptying and lasted about four hours.

Suction blister fluid was collected from blisters made by a Dermovac (Mediko Medical, Espoo, Finland) placed on the forearms of normal volunteers for 2–4 hr under a heat lamp as described by the manufacturer, after collection, all fluids were centrifuged (Microfuge II, Beckman) for 4 min at 11,600 g, and the supernatants were frozen at $-70°$ C. until use.

Collection of blood and preparation of plasma and serum

Blood samples were obtained from the antecubital vein of patients with chronic wounds and volunteers with suction blisters. The samples were drawn with a 21 gauge stainless steel needle attached to a blood collection device (Vacutainer, Becton Dickinson, Rutherford, N.J.) containing EDTA anticoagulant. To obtain plasma, cells were removed from the samples by centrifugation (1800 g for 15 min at $22°$ C. followed by 22,000 g for 30 min at $4°$ C.). The supernatants were filter sterilized using a 0.2 $\mu$m filter, and stored at $-70°$ C. until use. To obtain serum, $CaCl_2$ was added to samples at a final concentration of 14 mM. After 2 hours at $37°$ C., samples were clarified by centrifugation at 22,000 g for 30 min at $37°$ C. Supernatants were dialyzed overnight at $4°$ C. against Dulbecco's phosphate buffered saline (DPBS) (150 mM NaCl, 3 mM KCl, 1 mM $CaCl_2$, 0.5 mM $MgCl_2$, 1 mM $KH_2PO_4$, 6 mM $Na_2HPO_4$, pH 7.2), recentrifuged at 22,000 g for 30 min at $4°$ C., filter sterilized, and stored as above.

SDS-PAGE, cell blotting, and immunoblotting

Samples for electrophoresis were dissolved in reducing sample buffer (62.5 mM Tris-HCl, 2% SDS, 10% glycerol, 0.01% bromophenol blue, pH 6.8, 5% mercaptoethanol) unless indicated otherwise and subjected to electrophoresis in a 4 to 16% acrylamide slab gel containing a gradient of 3M to 8M urea (Jarvik, et al., 1980, J. Cell Biol. 85:258, 272). Purified fibronectin was 0.2 $\mu$g/lane for immunoblotting and 0.15 $\mu$g/lane for cell blotting. Purified vitronectin was 1 $\mu$g/lane for immunoblotting and 0.5 $\mu$g/lane for cell blotting. Wound fluid samples, plasma, and serum were 150 $\mu$g per lane for immunoblotting and 200 $\mu$g per lane for cell blotting (see below). Protein concentrations were determined by the Lowry method (Lowry, et al., 1951, J. Biol. Chem., 193:265–275).

For immunoblotting, proteins were transferred to nitrocellulose paper (Schleicher & Schuell) by electrophoresis at $4°$ C. for 1.5 hours at 150 mA followed by 1.5 hours at 300 mA similarly as described previously (see Example 1 and Wysocki et al., 1990, Lab Invest. 63:825–831). The transferred proteins were incubated with polyclonal or monoclonal antibodies for 2 hr at $22°$ C. followed by incubation with alkaline phosphatase conjugated goat anti-rabbit IgG or anti-mouse IgG (Bio-Rad, Richmond, Calif.) for 1 hr at $22°$ C. Visualization was accomplished using alkaline phosphatase conjugate substrate kit according to the manufacturer's instructions.

For cell blotting, proteins were transferred to nitrocellulose paper as above. The transferred protein strips were blocked with 3% BSA (Miles, Fraction V) in TBS (20 mM tris base, 0.5M NaCl, pH 7.5), then washed with TTBS (TBS+0.05% Tween 20) followed by DPBS. BHK cells were radiolabeled metabolically in culture medium overnight with 20 $\mu$Ci/ml of $^3$S-methionine (ICN, ~1100 Ci/mole) in methionine-deficient MEM (Flow Labs) supplemented with 10% tryptose phosphate, 10% fetal bovine serum (FBS)(Sigma), 1× L-glutamine, 20 mM hepes). Radiolabeled cells were harvested by trypsinization and cultured 3-4 hr in suspension in the fresh medium without radiolabeled methionine prior to use. Each nitrocellulose strip was incubated with about $10^6$ cells/$3.25 \times 10^6$ cpm in 0.5 ml DPBS containing 30 mg/ml bovine serum albumin (Miles, Fraction V) for 1 hr at 37° C., after which non-attached cells were removed by washing 3 times with TTBS. Each wash lasted 5 min during which the samples were subjected to 100 strokes/min on a reciprocating shaker (New Brunswick R76). The samples were fixed with 3% paraformaldehyde and dried for autoradiography.

Scanning Electron Microscopy

Cells attached to nitrocellulose were observed by scanning electron microscopy using the osmium impregnation and hexamethyldisilazane air drying method (Lee et al., 1989, J. Cell Biol., 109:308a). After the final TTBS wash, nitrocellulose strips were rinsed in 0.1M cacodylate buffer with 0.1M sucrose and cut into pieces. Samples were fixed in freshly prepared 2% glutaraldehyde, 4% paraformaldehyde, and 1% tannic acid in 0.1 M cacodylate buffer with 0.1M sucrose overnight at 4° C. Samples were postfixed in 0.1 % osmium tetroxide in the same buffer for 1 h at room temperature. After washing in double distilled water, samples were further subjected to two cycles of 1% aqueous thiocarbohydrazide (Sigma, St. Louis, Mo.) and 1% osmium tetroxide in distilled water, 15 min for each step. Samples were then dehydrated through series of graded ethanol solutions (70%, 90%, 95%, and 100%), 5 min for each step. To ensure complete dehydration, the final dehydration step was carried out by immersing samples for 15 minutes in absolute ethanol taken from a freshly opened bottle. Hexamethyldisilazane (Sigma, St. Louis, Mo.) was added to samples in a gradual fashion to replace absolute ethanol, 1:1, 2:1, then pure hexamethyldisilazane, 5 min for each step. Samples were air dried directly from hexamethyldisilazane and mounted on stubs by using colloidal graphite. Mounted samples were viewed without metal coating in JEOL 840 scanning electron microscope and photographed with Polaroid type 55 films.

Cell Attachment Assay

Cell attachment was measured as described previously (Grinnell et al., 1988, J. Cell Sci., 90:201-214). BHK cells were radiolabeled metabolically for 4 hr in growth medium containing 1% FBS and 2.5 uCi/ml of $^3$H-labeled L-leucine (Amersham, 343 mCi/mg). Radiolabeled cells ($7 \times 10^4$) were washed and resuspended in 0.175 ml DPBS with serum or wound fluid as indicated and incubated for 45 min at 37° C. in 48-well tissue culture dishes (Costar). Before adding the cells, culture dishes were coated with an air-dried film of gelatin (0.05 ml, 1 mg/ml gelatin in 0.1M HAc, air-dried at 37° C.) and treated with serum or wound fluid as indicated for 20 min at 37° C. At the end of the incubations, the dishes were subjected to shaking for 10 sec at 150 rev/min on a New Brunswick R-2 reciprocating shaker. Cells resuspended by this procedure were removed with a pipette. The cells remaining attached to the dishes were solubilized with 0.175 ml of 2% sodium dodecyl sulphate. Samples of nonattached and attached cells were mixed with 10 ml of Budget Solve (RPI Corp.), radioactivity was measured in a Beckman scintillation spectrophotometer, and the percentage of attached cells calculated.

Fibronectin, vitronectin, and adhesion proteins in plasma, serum, and suction blister fluid In the following experiments, fibronectin, vitronectin, and adhesion proteins were compared in acute wound fluid (suction blister fluid, 3 volunteers; mastectomy fluid, 5 patients) and chronic wound fluid (venous stasis ulcers, 11 patients). Controls were plasma and serum obtained at the same time that suction blister fluid and chronic wound fluid was collected. Immunoblotting was used to analyze fibronectin and vitronectin in the various samples and cell blotting to analyze adhesion proteins. With the cell blotting method (FIG. 6), polypeptides were transferred from SDS-PAGE gels to nitrocellulose, and the nitrocellulose was incubated at 37° C. with radiolabeled BHK cells. Using immunoblotting with polyclonal antibodies and cell blotting, fibronectin, vitronectin, and adhesion protein profiles were compared in human plasma (P), serum (S), and suction blister fluid (B). In cell blotting, polypeptides were transferred to nitrocellulose paper and detected by incubation with radiolabeled BHK cells followed by autoradiography. Controls included purified human fibronectin (F) and vitronectin (V). Fibronectin, vitronectin, and adhesion protein profiles were similar in plasma, serum, and suction blister fluid.

At the end of the assay, the unattached cells were washed away. The attached cells were fixed and visualized by autoradiography as radioactive bands, thereby showing the locations of adhesion-promoting polypeptides. SEM observations confirmed that cells attached and spread partially on adhesion proteins transferred to nitrocellulose (FIG. 7), and in duplicate samples, results of SEM observations and autoradiography corresponded closely.

Figure 6:
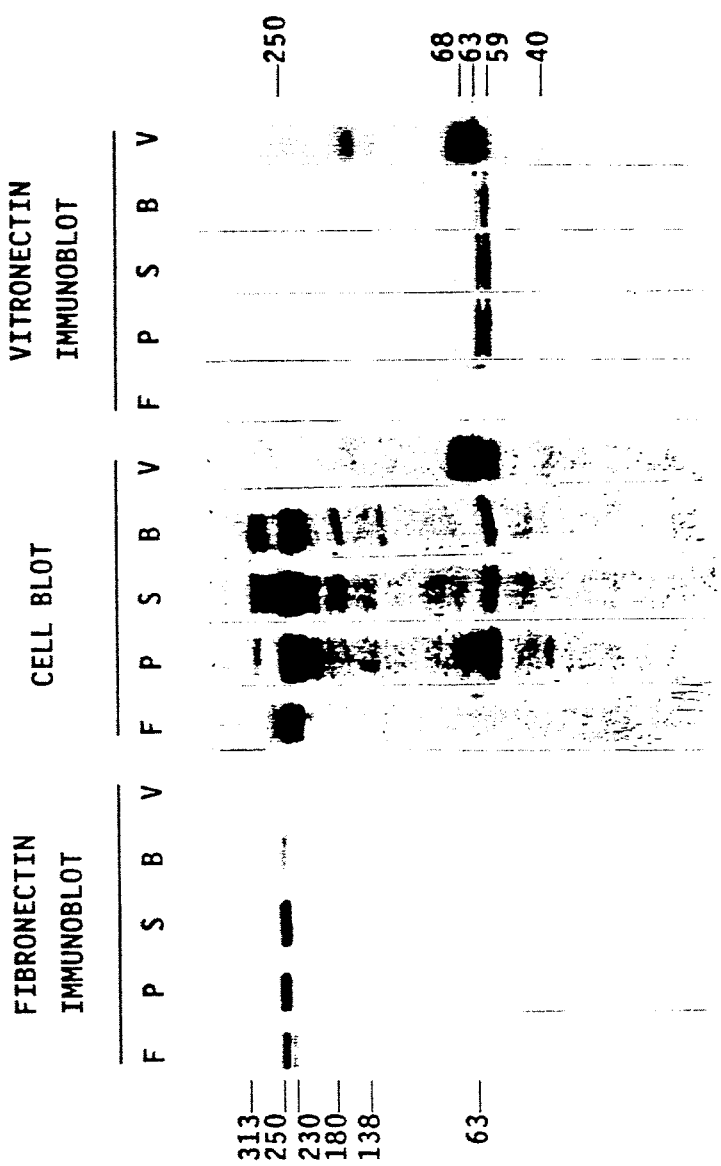
FIG. 6 shows: Fibronectin (F), vitronectin (V), and adhesion proteins in plasma (P), serum (S), and suction blister fluid (B).

SEM observations ($\times 200$) of samples from FIG. 6 confirmed that BHK cells attached and spread partially on adhesion proteins transferred to nitrocellulose. Regions shown correspond to the major fibronectin bands detected by immunoblotting of fibronectin standard and serum. Addition of GRGDSP (0.5 mg/ml) with radiolabeled BHK cells resulted in decreased cell attachment and inhibition of spreading.

FIG. 6 shows immunoblotting and cell blotting experiments with plasma (P), serum (S), and suction blister fluid (B), all from the same person. Samples loaded on the gels contained the same amounts of protein (150 μg/lane for immunoblotting and 200 μg/lane for cell blotting). Standard lanes contained purified human fibronectin (F) and vitronectin (V). Anti-fibronectin reacted with fibronectin but not vitronectin, and anti-vitronectin reacted with vitronectin but not fibronectin. Under the assay conditions used, cell blotting was as sensitive as immunoblotting.

Figure 10:
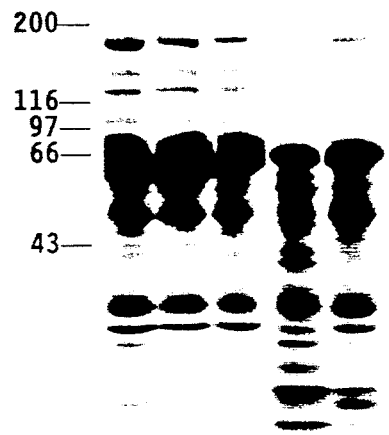
FIG. 10 shows protein profiles in chronic wound fluid (WFA and WFB), mastectomy fluid, and suction blister fluid.

Fibronectin, vitronectin, and adhesion protein profiles were similar in plasma, serum, and suction blister fluid. (Coomassie blue profiles for serum and suction blister fluid are shown in FIG. 10.) Coomassie blue staining showed that the overall protein profile of serum and wound fluid was similar, but most of the high molecular weight polypeptides evident in serum (S), suction blister fluid (B), and mastectomy fluid (M) were absent or substantially reduced in wound fluid type A (WFA), which contained a variety of lower molecular weight polypeptides. Also, there was a decrease in high molecular weight polypeptides in wound fluid type B (WFB).

The major fibronectin component migrated around 250 kDa in the immunoblotting assay, and a component of the same size was detected by cell blotting. Also, a 230 kDa fibronectin fragment was detected by immunoblotting and by cell blotting. Vitronectin appeared as an about 60 kDa doublet by immunoblotting or cell blotting. This doublet probably corresponds to the 75 and 65 kDa vitronectins (Barnes et al., 1983, J. Biol. Chem. 258:12548-12552), which apparently were compressed beneath the large albumin band. Vitronectin purified from outdated human blood showed higher molecular weight components including a third polypeptide, probably the 57 kDa thrombin fragment (Silnutzer et al., 1984, Biochem. Biophys. Res. Commun. 118:339-343). Sometimes, but not always, anti-vitronectin antibodies and cell blotting also indicated the presence of a 40 kDa component. Fibronectin and vitronectin were the major cell adhesion proteins in acute wound fluid which could be detected by BHK cells.

Figure 8:
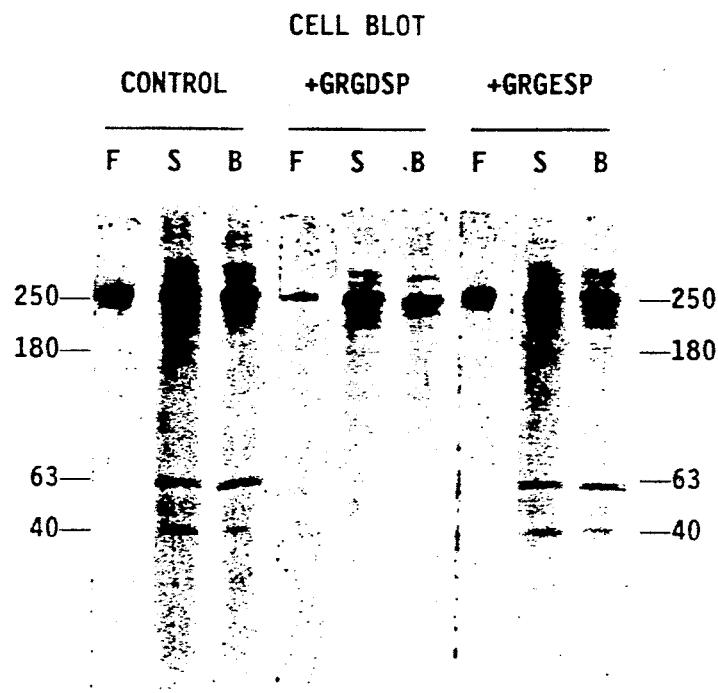
FIG. 8 shows the effect of GRGDSP and GRGESP on cell blotting.

There were also a number of minor adhesion-promoting polypeptides in blood and wound fluid. One group with molecular masses >250 kDa was more apparent in serum and blister fluid than in plasma. If the immunoblots were overdeveloped, then the higher molecular mass bands stained with anti-fibronectin antibodies (see Example 1 and Wysocki et al., 1990, Lab Invest. 63:825-831). To determine if the adhesion promoting peptides promoted adhesion through an RGD cell binding domain (Ruoslahti et al., 1987, Science 238:491-497), the effects of RGD-containing peptides were tested on their activity. FIG. 8 shows that cell attachment to vitronectin could be inhibited completely by the active cell adhesion peptide GRGDSP, whereas the control peptide GRGESP had no effect. Samples of fibronectin (F), serum (S), and blister fluid (B) were subjected to cell blotting. In the lanes indicated, the peptides GRGDSP (0.5 mg/ml) or GRGESP (0.5 mg/ml) were added to the incubations with radiolabeled BHK cells. GRGDS completely inhibited cell attachment to vitronectin and markedly reduced cell attachment to fibronectin.

Figure 7:
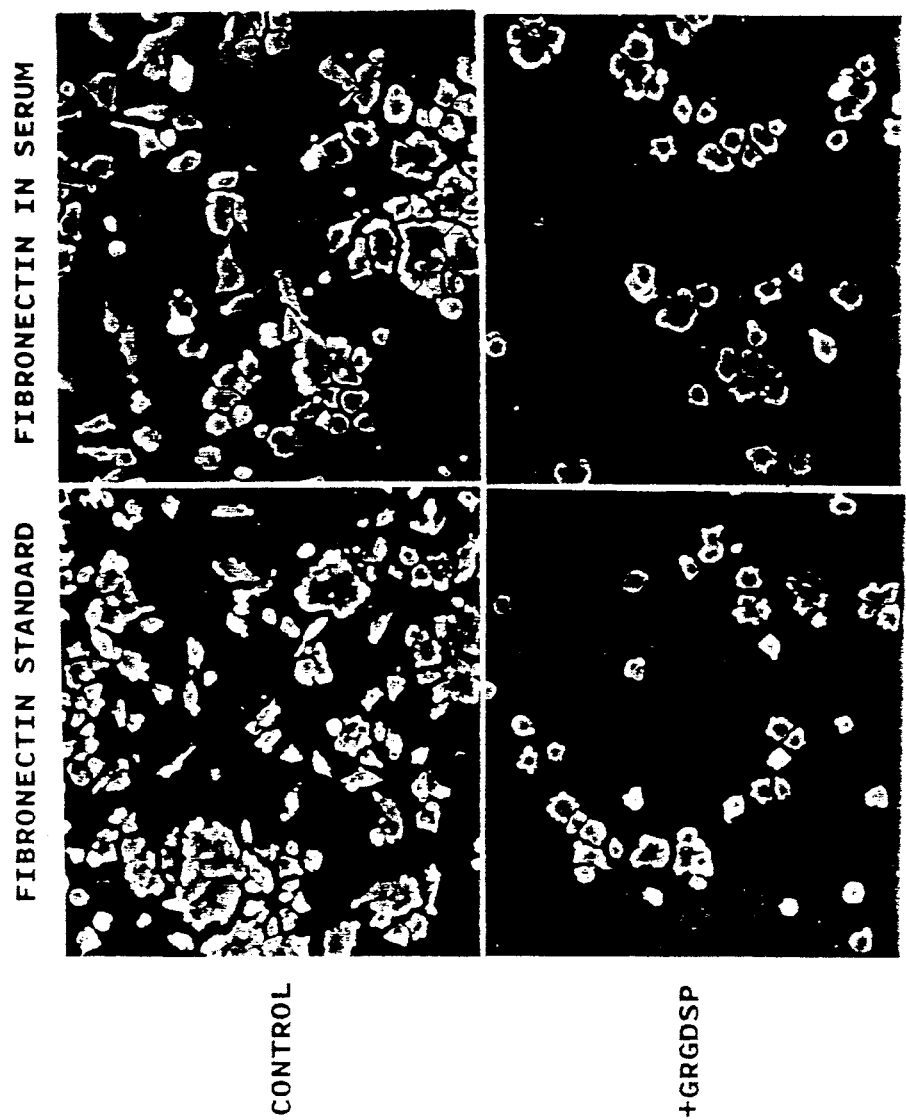
FIG. 7 shows an observation of BHK cell blots by SEM.

GRGDSP also decreased cell attachment to fibronectin and the higher molecular weight polypeptides. Even though attachment was not completely inhibited, those cells that did attach were unable to spread (FIG. 7). Based on these results, it appears that the >250 kDa polypeptides are covalently-crosslinked fibronectin complexes that form in small amounts during blood clotting.

Figure 9:
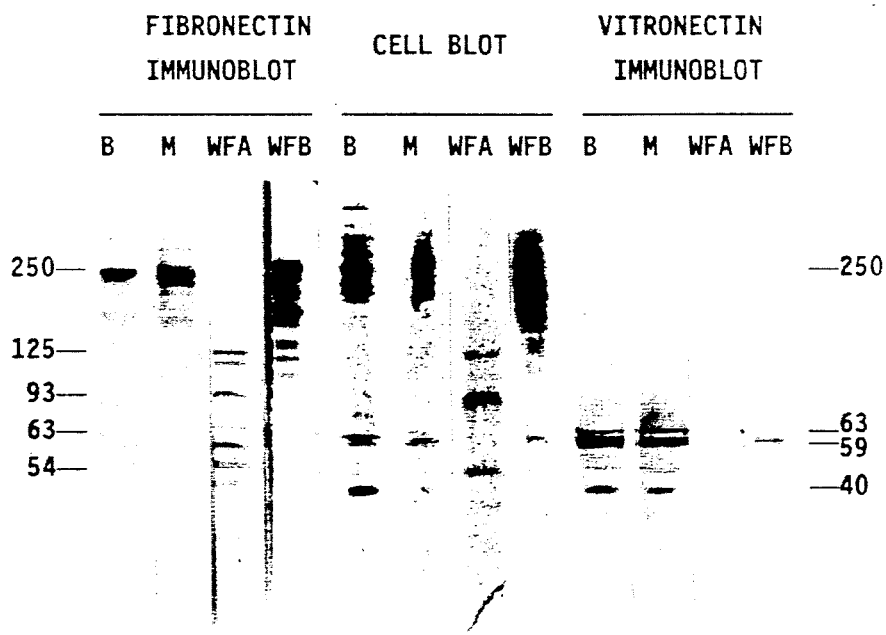
FIG. 9 shows fibronectin, vitronectin, and adhesion proteins in chronic wound fluid (WFA and WFB), mastectomy fluid (M), and suction blister fluid (B).

Fibronectin, vitronectin, and adhesion proteins in chronic wound fluid, mastectomy fluid, and suction blister fluid FIG. 9 compares the profiles of fibronectin, vitronectin, and adhesion proteins in suction blister fluid (B), mastectomy fluid (M), and wound fluid obtained from chronic stasis ulcers. FIG. 5 shows corresponding Coomassie blue profiles for mastectomy fluid and stasis ulcer samples. Samples contained the same amounts of protein (150 μg/lane for immunoblotting or Coomassie blue staining and 200 μg/lane for cell blotting). Wound fluids from chronic stasis ulcers showed two different patterns that will be described below, which were arbitrarily designated type A (WFA) and type B (WFB). Of the 11 patients' chronic wound fluids that were examined, 3 were type A and 8 were type B.

Immunoblotting and cell blotting were used to compare the profiles of fibronectin, vitronectin, and adhesion proteins in wound fluid from chronic stasis ulcers (WFA and WFB), mastectomy fluid (M), and suction blister fluid (B). Type A chronic wound fluid (3/11 patients) showed degradation of intact fibronectin to numerous fragments ranging from 30-125 kDa. Some fibronectin fragments, 54 kDa, 93 kDa, and 125 kDa, showed cell binding activity. Also, vitronectin was completely degraded in type A wound fluid. Type B wound fluid (8/II patients) contained a mixture of fibronectin, vitronectin, and proteolytic fragments. Mastectomy fluid, like suction blister fluid, contained mostly intact fibronectin and vitronectin.

A characteristic feature of type A wound fluid was degradation of all intact fibronectin into numerous fragments ranging from 30 to 125 kDa. Some fibronectin fragments, 54 kDa, 93 kDa, and 125 kDa, showed cell binding activity. Also, vitronectin was completely degraded in type A wound fluid. In marked contrast, type B wound fluid contained a mixture of fibronectin, vitronectin, and proteolytic fragments. Mastectomy fluid, like suction blister fluid, contained mostly intact fibronectin and vitronectin and showed minimal degradation. The immunoblotting results were consistent with results obtained by staining gels with Coomassie blue (FIG. 10). High molecular weight polypeptides evident in serum (S), suction blister fluid (B), and mastectomy fluid (M) were absent or substantially reduced in type A wound fluid. The latter, however, contained a variety of lower molecular weight polypeptides. Also, there was a decrease in high molecular weight polypeptides in type B wound fluid.

Figure 11:
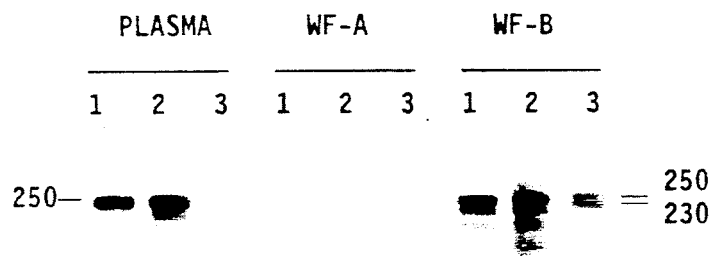
FIG. 11 shows an analysis of fibronectin and fibronectin fragments in wound fluid.

FIG. 11 provides additional information about fibronectin and fibronectin fragments in type A and type B wound fluids. In lane 1, samples were immunoblotted with monoclonal antibodies that bind near fibronectin's RGD cell attachment domain, whereas samples in lane 2 were immunoblotted with polyclonal anti-fibronectin antibodies as for FIG. 9. In type A wound fluid only the three fragments that had cell attachment activity, 125 kDa, 93 kDa, and 54 kDa, were detected by the anti-cell binding domain antibodies. Consistent with this observation, cell adhesion to these fragments was inhibited by 0.5 mg/ml GRGDSP.

Samples of serum and chronic wound fluid were immunoblotted as follows: lane 1, monoclonal antibodies that bind near fibronectin's RGD cell attachment domain; lane 2, polyclonal anti-fibronectin antibodies; lane 3, monoclonal antibodies against the alternatively spliced ED-A domain of fibronectin. In wound fluid type A, the three fragments with cell attachment activity, 125 kDa, 93 kDa, and 54 kDa, were detected by the anti-cell binding domain antibodies. Fibronectin in serum and fibronectin degradation fragments did not contain the ED-A domain, but his domain was found in intact fibronectin in wound fluid type B.

In lane 3 of FIG. 11, samples were immunoblotted with monoclonal antibodies against the alternatively spliced ED-A domain of fibronectin, which is more prominent in cellular fibronectin than in plasma fibronectin (Borsi et al., 1987, J. Cell Biol. 104:595-600). In the samples from plasma, little staining of fibronectin by anti-ED-A was evident. But in wound fluid type B, where much of the fibronectin appeared intact or in large fragments, staining by anti-ED-A was strong, which indicated that chronic wound fluid contains substantial cellular fibronectin as well as plasma fibronectin. The ED-A domain was not present in the fragments remaining after extensive degradation of fibronectin in wound fluid type A.

Figure 12:
FIG. 12 shows an analysis of fibronectin in serum and wound fluid under reducing and non-reducing conditions.

Although fibronectin in wound fluid type B had 250 kDa subunits, these subunits were unable to form normal dimers. FIG. 12 shows that shifting the SDS-PAGE conditions from reducing to non-reducing sample buffer resulted in the formation of 440 kDa dimers by purified fibronectin or fibronectin in serum or suction blister fluid.

Samples of fibronectin, plasma, blister fluid, and type B wound fluid were subjected to SDS-PAGE under reducing and non-reducing (sample buffer without mercaptoethanol) conditions and then immunoblotted with anti-fibronectin antibodies. Formation of 440 kDa dimers occurred with purified fibronectin or fibronectin in serum or suction blister fluid, but not with fibronectin in type B wound fluid.

In type B wound fluid, however, the shift was much less pronounced, and most of the fibronectin did not form dimers. These results indicate that some fibronectin in type B wound fluid is degraded near the carboxy terminus, where the interchain disulfide bonds are located (Chen et al., 1977, Biochim. Biophys. Acta 493:310–322).

Figure 13:
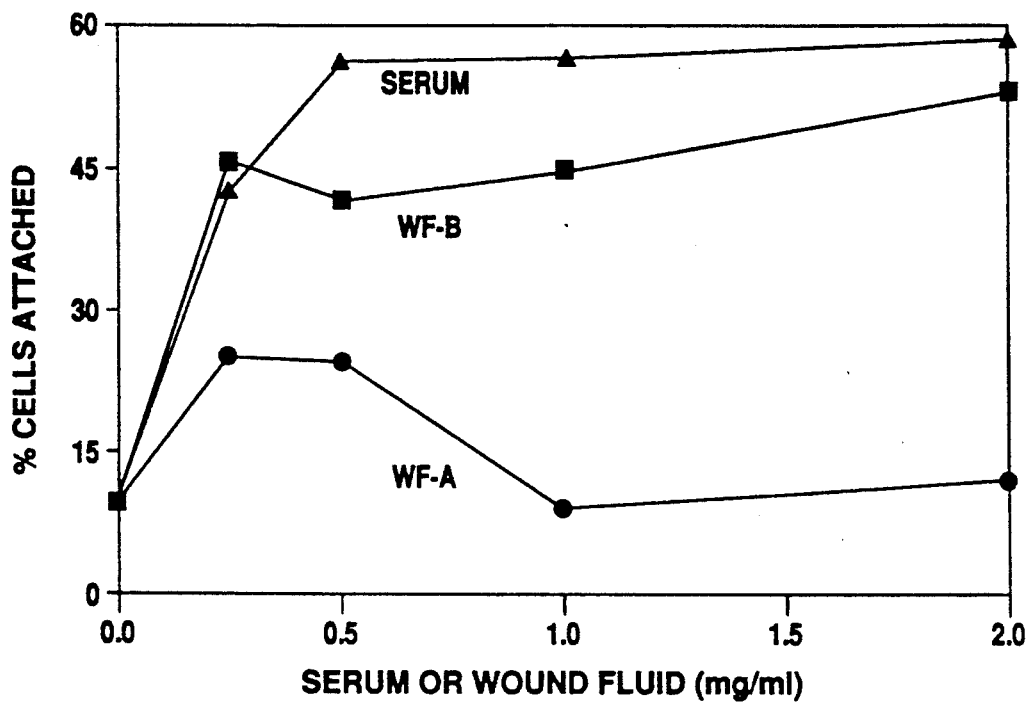
FIG. 13 shows the effect of chronic wound fluid on BHK cell attachment to gelatin.

Biological activity of adhesion proteins in chronic wound fluid compared to serum Degradation of adhesion proteins in wound beds could be an important factor in the inability of chronic wounds to close. It was of interest, therefore, to test the effect of wound fluid on cell adhesion. In the first series of experiments, cell adhesion to gelatin was measured. FIG. 13 shows results from an assay to measure adhesion-promoting activity of wound fluid compared to serum. Culture dishes were coated with gelatin, incubated with serum or chronic wound fluid at the concentrations indicated, and then incubated with radiolabeled BHK cells. Little cell attachment to gelatin occurred in the absence of added serum or wound fluid type B. Type A wound fluid showed little cell adhesion promoting activity.

Figure 14:
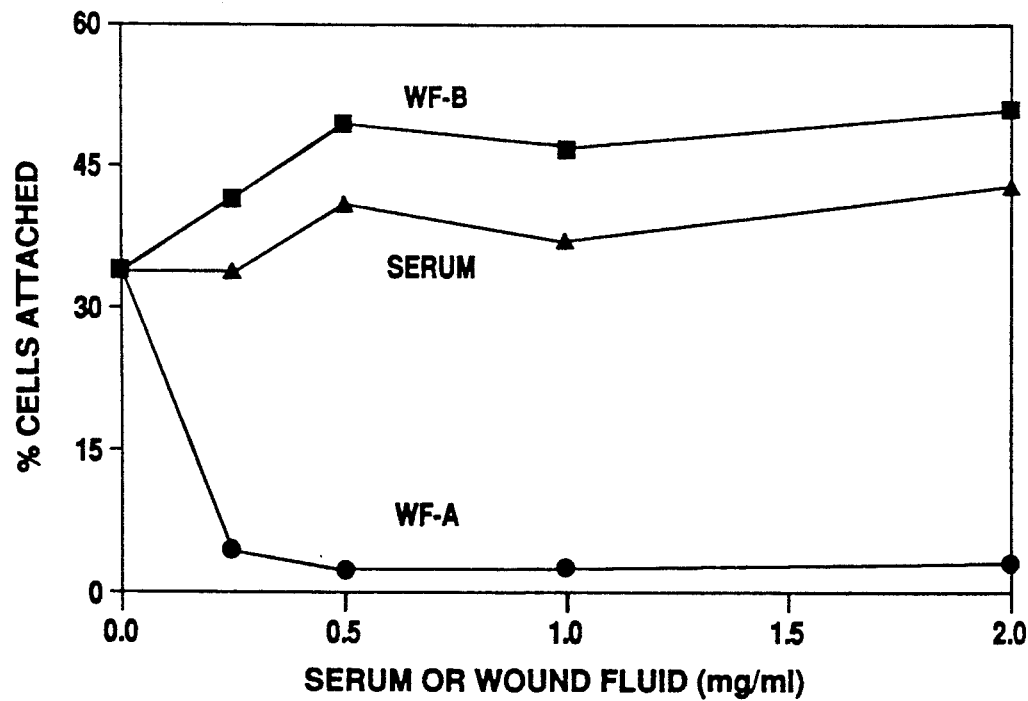
FIG. 14 shows the effect of chronic wound fluid on BHK cell attachment to serum-coated gelatin.

Little cell attachment to gelatin occurred in the absence of added serum or fluid. As the concentration of serum or wound fluid type B increased, the extent of cell adhesion increased. Since the total protein concentration in serum and wound fluids was similar, it appeared that adhesion proteins in wound fluid type B had biological activity equivalent to adhesion proteins in serum. The protein concentration required for complete activity in this assay, 0.5 mg/ml, corresponded to about 1% serum or wound fluid. On the other hand, wound fluid type A showed little cell adhesion-promoting activity. FIG. 14 shows a parallel experiment that was designed to detect adhesion-inhibiting activity. Culture dishes were coated with gelatin, then with serum (2 mg/ml), and then incubated with radiolabeled BHK cells in medium containing serum or chronic wound fluid at the concentrations indicated. Addition of type A wound fluid resulted in a dose-dependent inhibition of attachment. Here, substrata were previously coated with gelatin and then with 2.0 mg/ml serum. Addition of more serum or type B wound fluid with the cells did not affect their attachment to gelatin, but addition of type A wound fluid resulted in dose-dependent inhibition at a concentration.

Figure 15A:
FIG. 15 shows the reversibility and neutralization of type A wound fluid by fetal bovine serum.
Figure 15B:
Figure 15C:
Figure 15D:
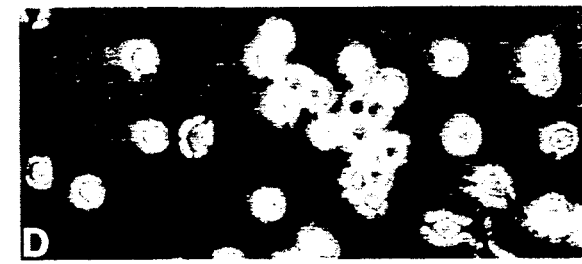
Figure 15E:

The effects of type A wound fluid may have resulted from an absence of intact adhesion proteins or the presence of protease activity in the wound fluid (see Example 1 and Wysocki et al., 1990, Lab Invest. 63:825–831). To distinguish between these possibilities, 0.5 mg/ml type A wound fluid (protein equivalent to 1% serum) was mixed with excess fibronectin (100 μg/ml) or fetal bovine serum (10%, about 4 mg/ml), and then the activity of the wound fluid tested (see FIG. 15A–15E). Culture dishes were coated with fibronectin (10 μg/ml) and then incubated 2 hr with BHK cells in DMEM and 10% fetal bovine serum (~4 mg/ml protein). Complete cell spreading occurred (see FIG. 15A). The medium was replaced with DMEM and 0.5 mg/ml type A wound fluid, and the incubations continued for an additional 90 min, during which the cells rounded up (see FIG. 15B). Wound fluid was removed and DMEM with 10% fetal bovine serum added and incubated with the cells for another 2 hr, during which the cells re-spread (see FIG. 15C). Addition of 100 μg/ml fibronectin with wound fluid had no effect (see FIG. 15D). Addition of 10% FBS with wound fluid neutralized the cell rounding activity. Inhibition was completely neutralized by 10% fetal bovine serum (see FIG. 15E) but not by 100 μg/ml fibronectin. These results show that the effects of wound fluid type A are reversible and can be neutralized by excess serum, which contains diverse protease inhibitors, but not by excess fibronectin. Therefore, it appears that type A wound fluid may inhibit adhesion at least primarily because of the presence of active protease(s) in the wound fluid rather than because of the absence of intact adhesion proteins (although of course the former may lead to the latter).

While the present invention is susceptible to various modifications and alternative forms, specific embodiments thereof have been shown by way of examples and the Figures, and have been herein described in detail. It should be understood, however, that it is not intended to limit the invention to the particular forms disclosed but on the contrary, the claimed invention is to include all modifications, equivalents, and alternatives falling within the spirit and scope of the invention a defined by the appended claims.

What is claimed is:

1. A method for assisting in the diagnosis of a cutaneous ulcer in a human subject as being a non-healing cutaneous ulcer, the method comprising:
   reacting a fluid sample from an ulcer of a subject with an antibody specifically binding intact fibronectin, intact vitronectin or fragments thereof to produce a reacted sample; and
   detecting intact fibronectin, intact vitronectin or fragments thereof in the reacted sample
   wherein a non-healing cutaneous ulcer is suggested when the reacted sample contains a fibronectin or vitronectin fragment or is deficient of intact fibronectin or vitronectin.

2. The method of claim 1 wherein the antibody is from a polyclonal source.

3. The method of claim 1 wherein the antibody is monoclonal.

4. The method of claim 1 wherein said non-healing cutaneous ulcer is a venous stasis ulcer, diabetic ulcer, or decubitus ulcer.

5. The method of claim 1 wherein an immunoassay is used in the reacting step and the immunoassay includes the steps of:
   separating proteins and protein fragments of the fluid sample according to size; and treating said separated proteins and fragments with a first antibody specifically binding human vitronectin or fragments thereof;

and wherein the detecting step includes treating the reacted separated proteins and fragments with a labeled second antibody having specific binding affinity for said first antibody; and determining the presence of human vitronectin by observation of label on said second antibody.

6. The method of claim 5 wherein the second antibody is labeled with a chromophore, a radioisotope, a fluorescent compound or an enzyme catalyzing formation of observably colored product from a substrate.

7. The method of claim 6 wherein said fluorescent compound is fluorescein.

8. The method of claim 6 wherein said enzyme is peroxidase.

9. A method for assisting in the diagnosis of a cutaneous ulcer in a human subject as being a non-healing cutaneous ulcer comprising the steps of:
a) separating proteinaceous components of a fluid sample from a cutaneous ulcer of a human subject in a matrix according to size; and
b) treating said matrix with an antibody specifically binding human vitronectin or fragments thereof to show antibody-reactive proteins;
wherein a non-healing cutaneous ulcer is associated with an absence of vitronectin or presence of vitronectin fragments.

10. The method of claim 9 wherein said non-healing cutaneous ulcer is a venous stasis ulcer, a diabetic ulcer, or a decubitus ulcer.

11. The method of claim 9 wherein said antibody is radio-labeled.

12. The method of claim 9 wherein said antibody is labeled with a fluorescent compound.

13. The method of claim 12 wherein the fluorescent compound is fluorescein.

14. The method of claim 9 wherein said antibody is from a polyclonal source.

15. The method of claim 9 wherein said antibody is monoclonal.

16. A method for assisting the diagnosis of a cutaneous ulcer in a human subject as being a non-healing cutaneous ulcer, the method comprises the steps of:
a) separating proteinaceous components of a fluid sample associated with a cutaneous ulcer of a subject in a matrix according to size;
b) reacting said matrix with a first antibody specifically binding human vitronectin to form bound vitronectin;
c) detecting said bound vitronectin with a second antibody conjugated to a label, the second antibody specifically binding the first antibody;
wherein a non-healing cutaneous ulcer is characterized by an absence of human vitronectin or presence of nitronectin fragments.

17. The method of claim 16 wherein at least one of said first antibody and said second antibody is from a polyclonal source.

18. The method of claim 16 wherein at least one of said first antibody and said second antibody is monoclonal.

19. The method of claim 16 wherein step c) involves visualization of the label conjugated to the second antibody.

20. A method aiding the diagnosis of a cutaneous ulcer as a non-healing cutaneous ulcer in a human subject, the method comprising the steps of:
(a) separating proteins and protein fragments thereof present in a fluid sample associated with a cutaneous ulcer of a subject, said separating being on a basis of size;
b) detecting said separated proteins and protein fragments thereof by a process involving treatment with antibodies specifically binding human vitronectin, human fibronectin or fragments thereof; and
wherein a non-healing cutaneous ulcer is associated with a human vitronectin absence, human fibronectin absence or a presence of human fibronectin or human vitronectin fragments.

21. The method of claim 20 wherein said fluid sample is exudate from a cutaneous ulcer.

22. The method of claim 20 where in step (a) said separating involves electrophoresis.

23. The method of claim 22 wherein the electrophoresis is conducted in a gel.

24. The method of claim 20 wherein immediately prior to step (b) the method includes the additional step of:
a¹) transferring separated protein and protein fragments thereof to nitrocellulose paper;
and step b) is modified to comprise the steps of:
b¹) reacting said transferred protein and protein fragments thereof with a first antibody specifically binding human vitronectin, human fibronectin or fragments thereof; and
b²) incubating reacted human vitronectin, fibronectin or fragments thereof with a second antibody specifically binding said first antibody, said second antibody being conjugated to a peroxidase which forms a stain on contact with a chromophoric substrate.

25. The method of claim 20 wherein said human fibronectin fragments comprise at least one fragment having a molecular weight of 125 kDa, 93 kDa, 200 kDa, 116.5 kDa, 97 kDa, 66 kDa, or 43 kDa.

26. The method of claim 20 wherein said human fibronectin fragments comprise at least one fragment having a molecular weight of 125 kDa, or 93 kDa.

27. The method of claim 20 wherein said human fibronectin fragments are further defined as having a molecular weight of 125 kDa.

28. The method of claim 20 wherein said human vitronectin fragments are further defined as having a molecular weight of 40 kDa.

29. A method for aiding diagnosis of cutaneous ulcers as being non-healing cutaneous ulcers, the method comprising:
separating proteins and protein fragments associated with a cutaneous ulcer according to size;
placing separated proteins and protein fragments on a solid matrix;
incubating eukaryotic cells with the solid matrix in a cell culture medium; and
observing a pattern of cellular attachment to the solid matrix;
wherein a deficiency of cellular attachment or pattern of cellular attachment associated with fibronectin or nitronectin fragmentation characterizes a non-healing cutaneous ulcer.

30. The method of claim 29 wherein the cells are baby hamster kidney cells, normal rat kidney cells, melanoma cells or rat calvaria cells.

* * * * *

UNITED STATES PATENT AND TRADEMARK OFFICE
CERTIFICATE OF CORRECTION

PATENT NO.   :   5,270,168

DATED        :   December 14, 1993

INVENTOR(S)  :   Frederick Grinnell

It is certified that error appears in the above-identified patent and that said Letters Patent is hereby corrected as shown below:

```
In claim 29, column 28, line 63, please delete "nitronectin"
and insert therefor --vitronectin--.
```

Signed and Sealed this

Twenty-sixth Day of April, 1994

Attest:

BRUCE LEHMAN

*Attesting Officer*    *Commissioner of Patents and Trademarks*